US012618084B2

(12) United States Patent
Onishi

(10) Patent No.: US 12,618,084 B2
(45) Date of Patent: May 5, 2026

(54) METHOD FOR PRODUCING TRANSFORMANT

(71) Applicant: TOYOTA JIDOSHA KABUSHIKI KAISHA, Toyota (JP)

(72) Inventor: Toru Onishi, Toyota (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 1106 days.

(21) Appl. No.: 17/539,522

(22) Filed: Dec. 1, 2021

(65) Prior Publication Data

US 2022/0177927 A1     Jun. 9, 2022

(30) Foreign Application Priority Data

Dec. 3, 2020    (JP) ................................. 2020-200752

(51) Int. Cl.
*C12N 15/90* (2006.01)

(52) U.S. Cl.
CPC .................................. *C12N 15/905* (2013.01)

(58) Field of Classification Search
CPC .................................................. C12N 15/905
See application file for complete search history.

(56) References Cited

U.S. PATENT DOCUMENTS

| | | |
|---|---|---|
| 2015/0037892 A1 | 2/2015 | Wiessenhaan et al. |
| 2016/0017344 A1 | 1/2016 | Boeke et al. |
| 2020/0399659 A1 | 12/2020 | Onishi et al. |

FOREIGN PATENT DOCUMENTS

| | | | |
|---|---|---|---|
| JP | 2010-136627 A | 6/2010 | |
| JP | 2021-000041 A | 1/2021 | |
| WO | WO 2013/135728 A1 * | 9/2019 | ............. C12N 15/63 |

OTHER PUBLICATIONS

Kelly, et al. 2001. Genome-wide generation of yeast gene deletion strains. Comparative and Functional Genomics vol. 2, p. 236-242.*
Huang Yuanyuan et al., "Recombineering using RecET in Corynebacterium glutamicum ATCC14067 via a self-excisable cassette", Scientific Reports, vol. 7, No. 1, Dec. 1, 2017 (Dec. 1, 2017), XP055890282, DOI: 10.1038/s41598-017-08352-9; Retrieved from the Internet: URL:https://www.nature.com/articles/s41598-017-08352-9.pdf>.
Gietz, R. Daniel et al., "High-efficiency yeast transformation using the LiAc/SS carrier DNA/PEG method", Nature Protocols, vol. 2, No. 1, pp. 31-34, 2007.
Storici Francesca, et al., "Chromosomal site-specific double-strand breaks are efficiently targeted for repair by oligonucleotides in yeast", PNAS, vol. 100, No. 25, pp. 14994-14999, Dec. 9, 2003.

* cited by examiner

*Primary Examiner* — Anne M. Gussow
(74) *Attorney, Agent, or Firm* — Dinsmore & Shohl LLP

(57)     ABSTRACT

The present disclosure concerns evaluation as to whether or not a nucleic acid fragment having a target gene had been accurately integrated into the host genome. A group of nucleic acid fragments comprising a nucleic acid fragment having a target gene is introduced into host cells, and host cells in which the target gene had been cleaved from the genome DNA by the action of a site-specific recombinase are selected.

6 Claims, 15 Drawing Sheets

Specification includes a Sequence Listing.

[Fig. 1]
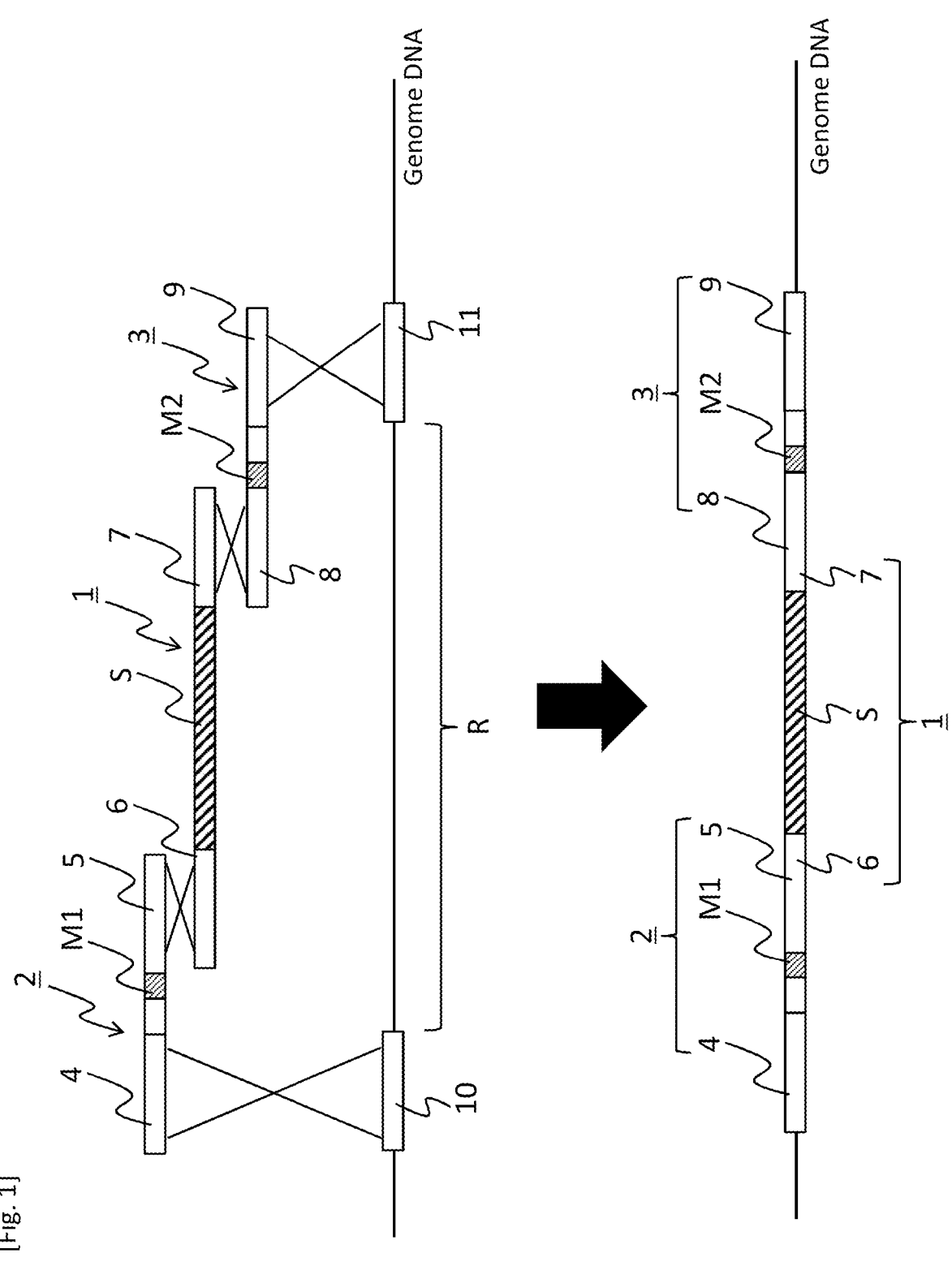

[Fig. 2]
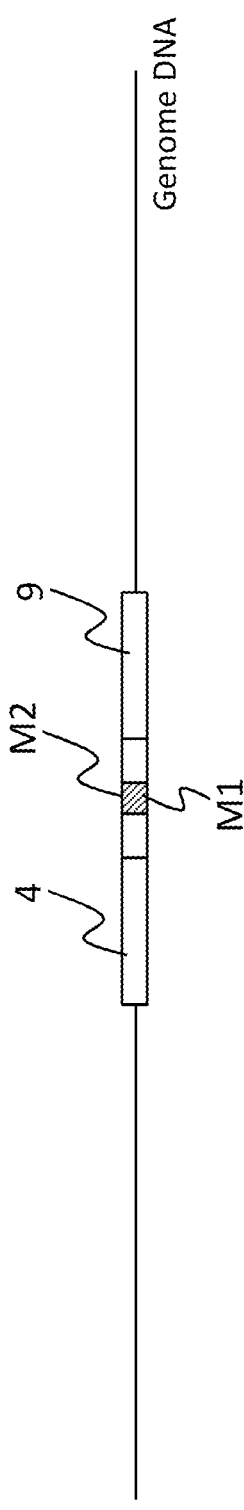

[Fig. 3]
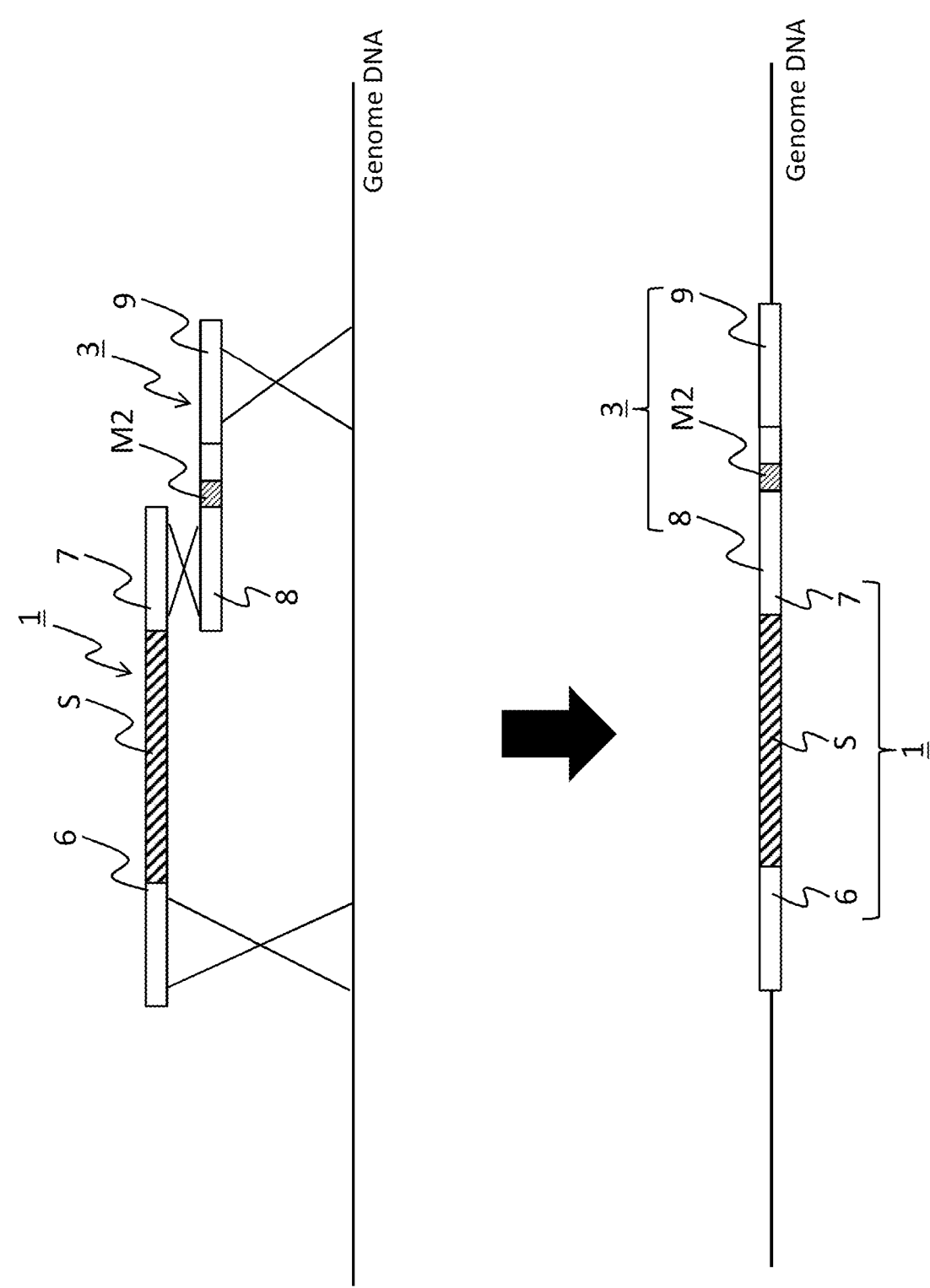

[Fig. 4]
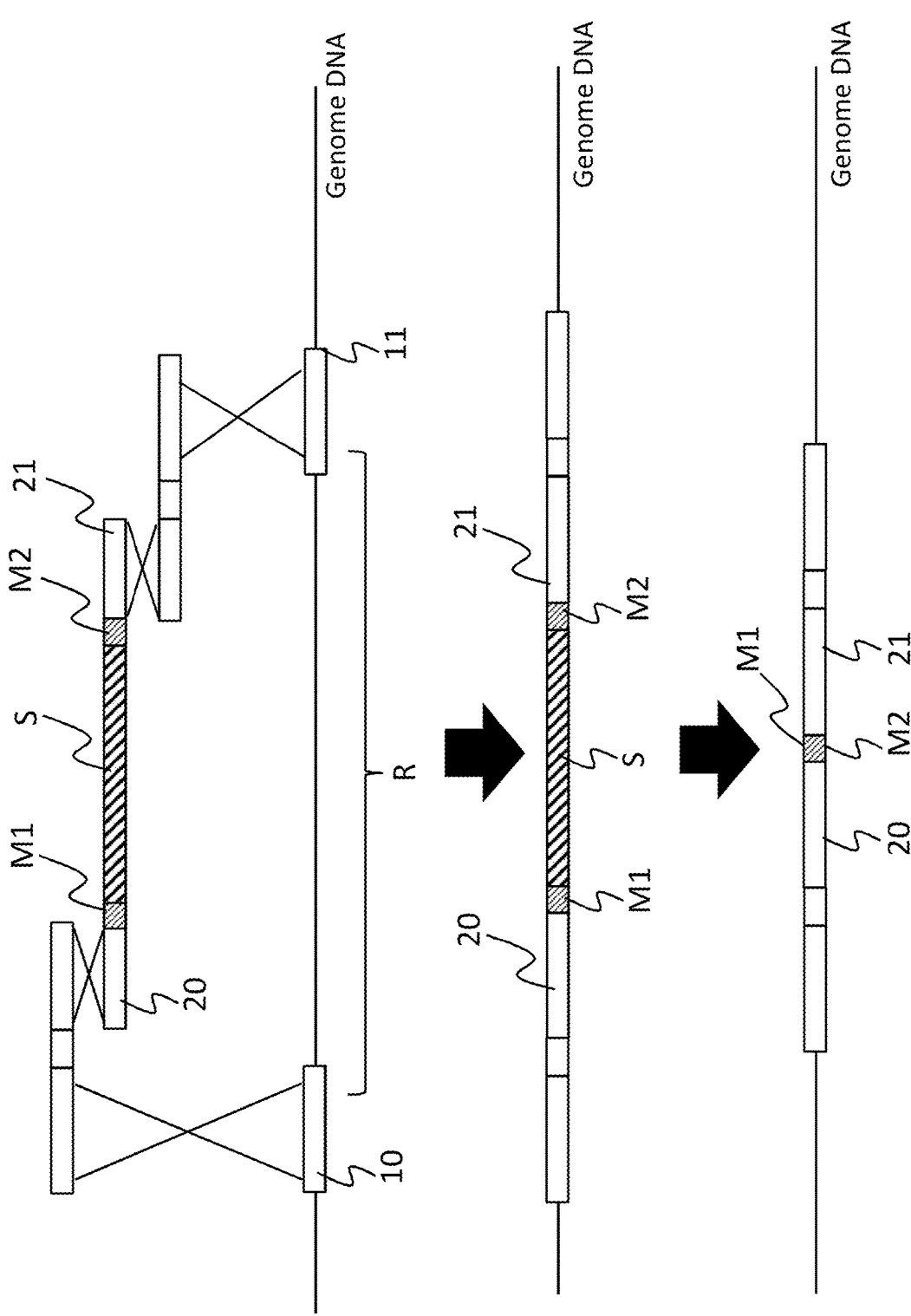

[Fig. 5]
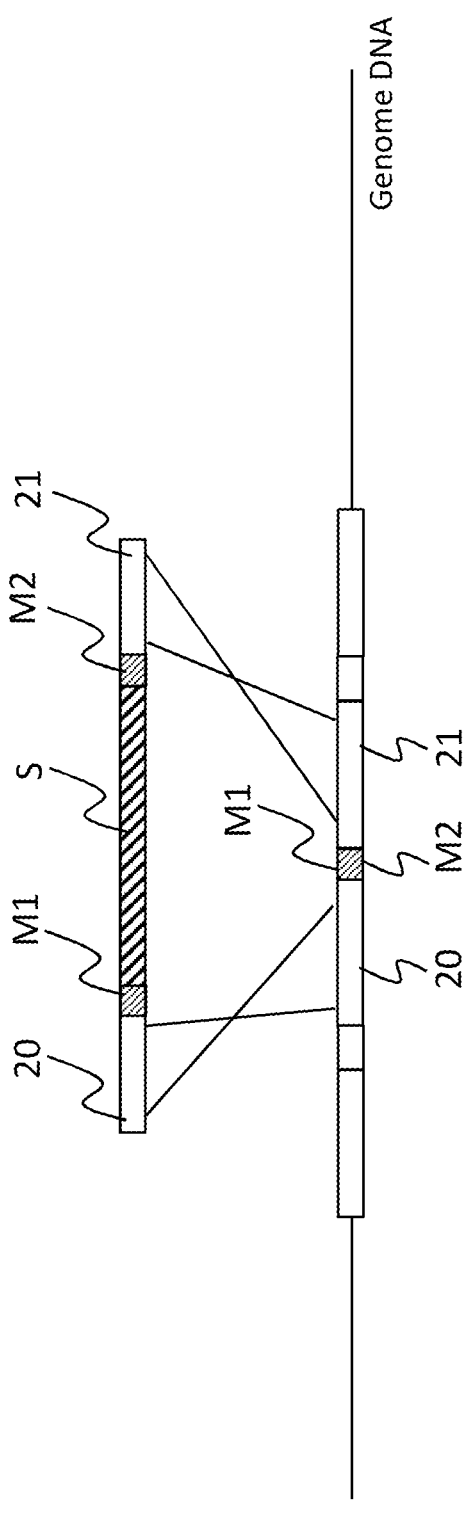

[Fig. 6]
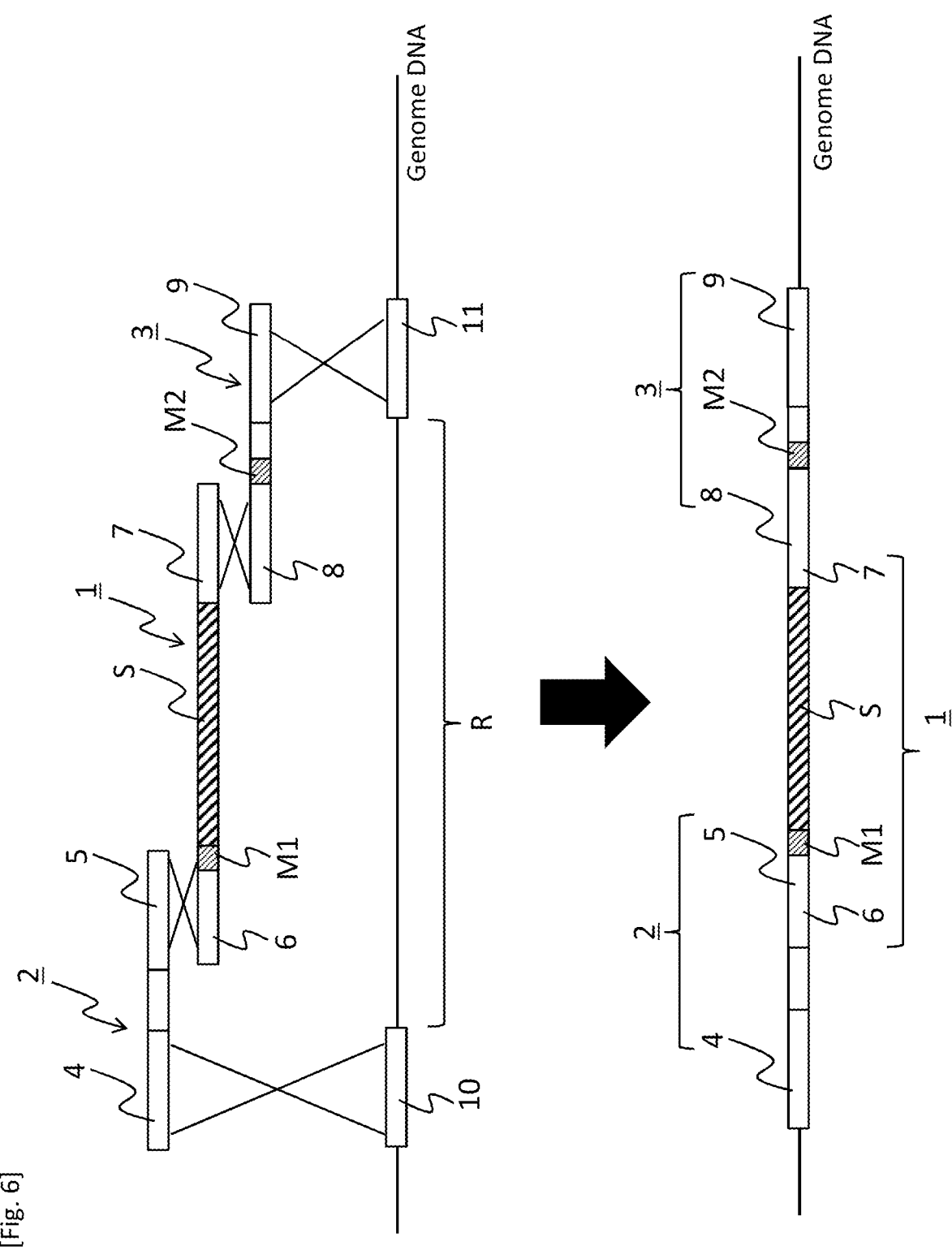

[Fig. 7]
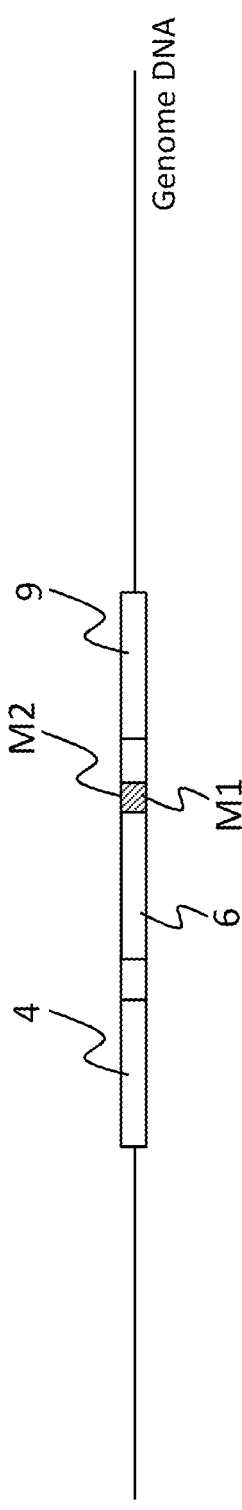

[Fig. 8]
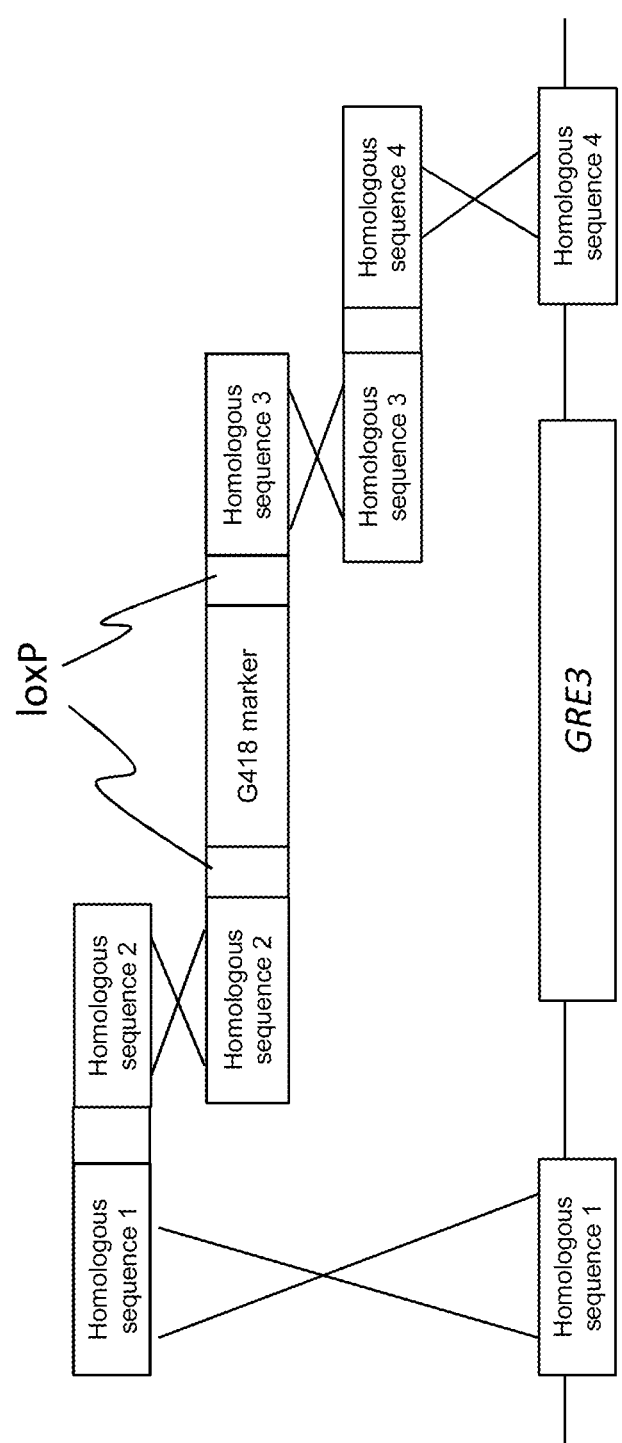

[Fig. 9]
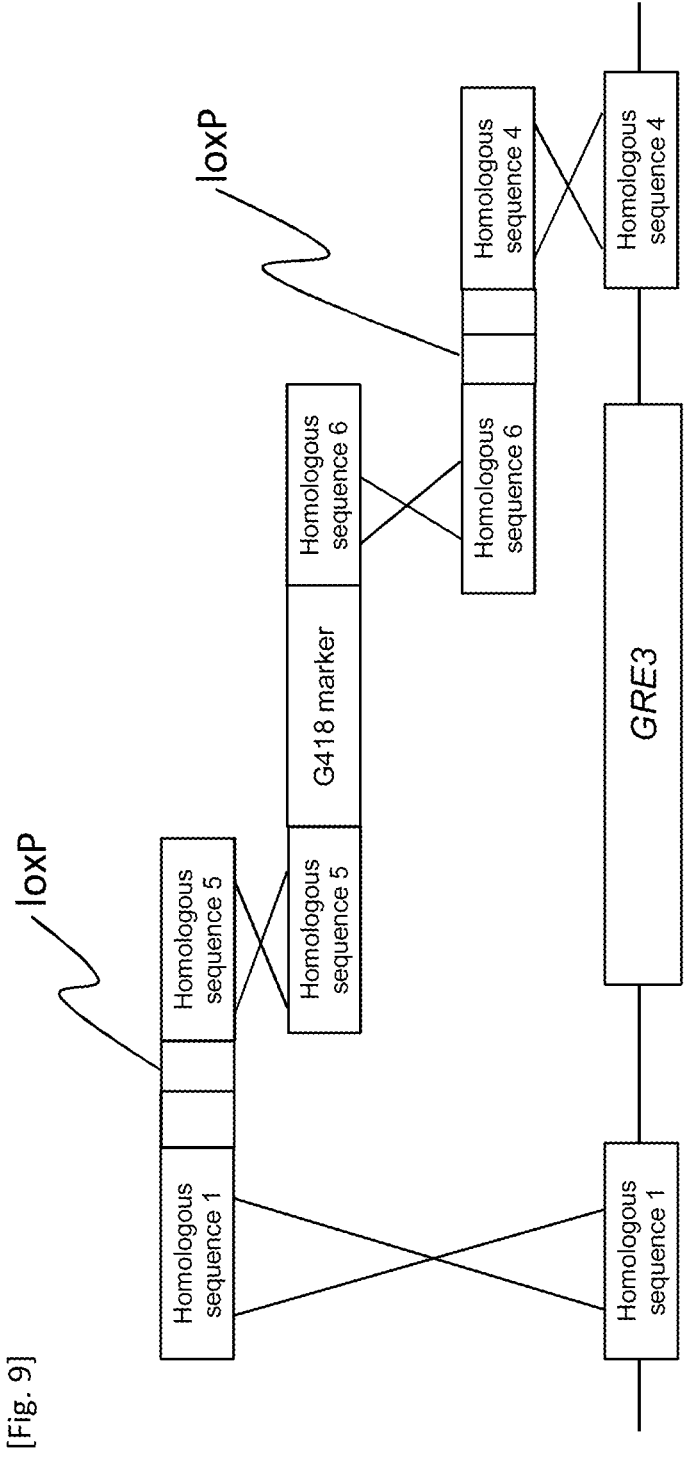

[Fig. 12]
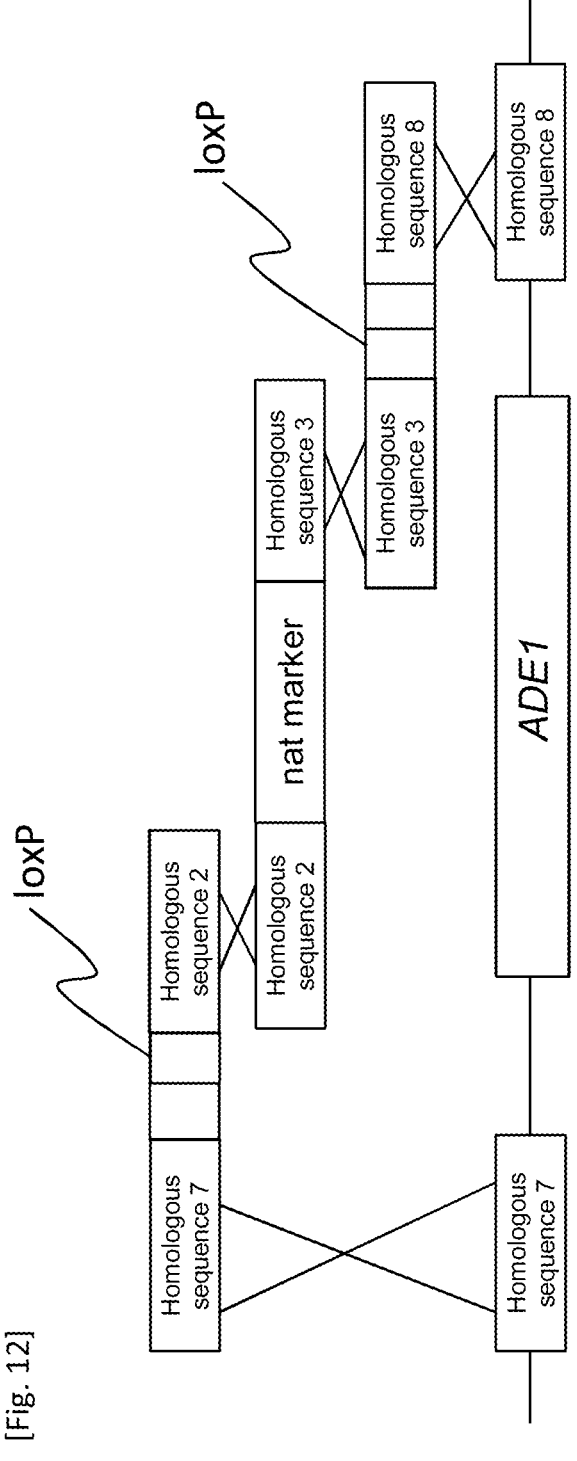

Figure 15:
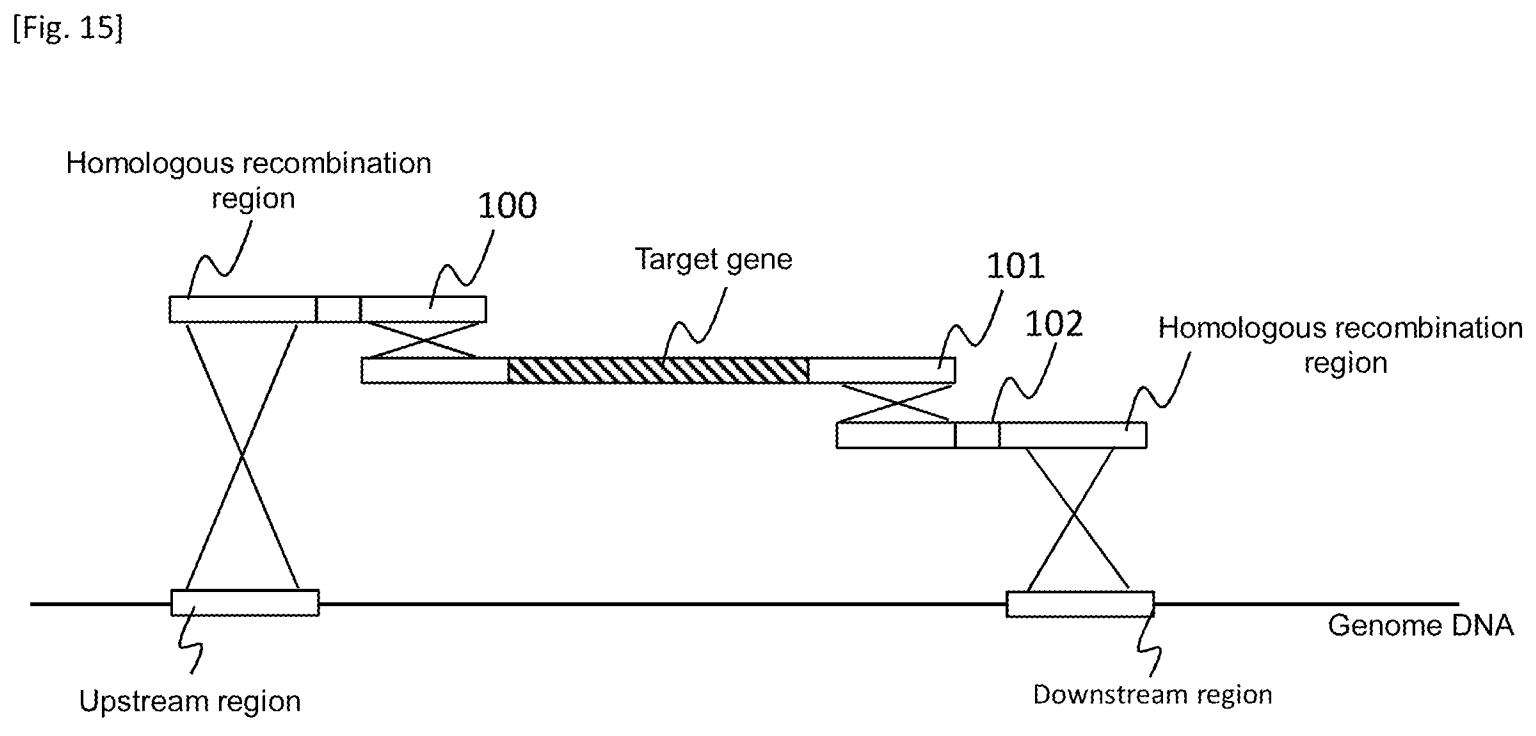

Homologous recombination region

Target gene

Homologous recombination region

100

101

102

Genome DNA

Downstream region

Upstream region

SEQUENCE LISTING

```
<160> NUMBER OF SEQ ID NOS: 144

<210> SEQ ID NO 1
<211> LENGTH: 68
<212> TYPE: DNA
<213> ORGANISM: Artificial
<220> FEATURE:
<223> OTHER INFORMATION: Synthetic DNA

<400> SEQUENCE: 1
gtggcccggg agagacagtt tagtagtgac tcgcggccag ttggggctaa acgagatttg        60
gaatattg                                                                 68

<210> SEQ ID NO 2
<211> LENGTH: 85
<212> TYPE: DNA
<213> ORGANISM: Artificial
<220> FEATURE:
<223> OTHER INFORMATION: Synthetic DNA

<400> SEQUENCE: 2
caatcacagg gcgggaaata agctacaatt aacgccaaaa aatctttaaa aaatttccaa        60 ttttcctta cgatttatat tacag                                               85

<210> SEQ ID NO 3
<211> LENGTH: 55
<212> TYPE: DNA
<213> ORGANISM: Artificial
<220> FEATURE:
<223> OTHER INFORMATION: Synthetic DNA

<400> SEQUENCE: 3
cccgccctgt gattgaggcg ggatggtgtc cccacagtca cgacgttgta aaacg            55

<210> SEQ ID NO 4
<211> LENGTH: 60
<212> TYPE: DNA
<213> ORGANISM: Artificial
<220> FEATURE:
<223> OTHER INFORMATION: Synthetic DNA

<400> SEQUENCE: 4
```

-continued

```
tctctcccgg gccacgacgc taggccagta cctccactct cagtacaatc tgctctgatg        60

<210> SEQ ID NO 5
<211> LENGTH: 77
<212> TYPE: DNA
<213> ORGANISM: Artificial
<220> FEATURE:
<223> OTHER INFORMATION: Synthetic DNA

<400> SEQUENCE: 5
gggatggtgt ccccacagtt accgttcgta tagcatacat tatacgaagt tatgtctctt        60
gcagaacaca ataagtg                                                      77

<210> SEQ ID NO 6
<211> LENGTH: 48
<212> TYPE: DNA
<213> ORGANISM: Artificial
<220> FEATURE:
<223> OTHER INFORMATION: Synthetic DNA

<400> SEQUENCE: 6
gttgaatatg gctcatcctt gtattactcg tttgttctgt ttctattc                    48

<210> SEQ ID NO 7
<211> LENGTH: 23
<212> TYPE: DNA
<213> ORGANISM: Artificial
<220> FEATURE:
<223> OTHER INFORMATION: Synthetic DNA

<400> SEQUENCE: 7
atgagccata ttcaacggga aac                                                23

<210> SEQ ID NO 8
<211> LENGTH: 38
<212> TYPE: DNA
<213> ORGANISM: Artificial
<220> FEATURE:
<223> OTHER INFORMATION: Synthetic DNA

<400> SEQUENCE: 8
tttagtagac atgcattaca accaattaac caattctg                                38

<210> SEQ ID NO 9
<211> LENGTH: 37
<212> TYPE: DNA
<213> ORGANISM: Artificial
<220> FEATURE:
<223> OTHER INFORMATION: Synthetic DNA

<400> SEQUENCE: 9
tgcatgtcta ctaaactcac aaattagagc ttcaatt                                 37

<210> SEQ ID NO 10
<211> LENGTH: 32
<212> TYPE: DNA
<213> ORGANISM: Artificial
<220> FEATURE:
<223> OTHER INFORMATION: Synthetic DNA

<400> SEQUENCE: 10
gggtaataac tgatataatt aaattgaagc tc                                      32

<210> SEQ ID NO 11
```

```
<211> LENGTH: 37
<212> TYPE: DNA
<213> ORGANISM: Artificial
<220> FEATURE:
<223> OTHER INFORMATION: Synthetic DNA

<400> SEQUENCE: 11
tatcagttat tacccagctt gcaaattaaa gccttcg                              37

<210> SEQ ID NO 12
<211> LENGTH: 26
<212> TYPE: DNA
<213> ORGANISM: Artificial
<220> FEATURE:
<223> OTHER INFORMATION: Synthetic DNA

<400> SEQUENCE: 12
ttagttatgt cacgcttaca ttcacg                                         26

<210> SEQ ID NO 13
<211> LENGTH: 38
<212> TYPE: DNA
<213> ORGANISM: Artificial
<220> FEATURE:
<223> OTHER INFORMATION: Synthetic DNA

<400> SEQUENCE: 13
gcgtgacata actaatcaat caccatcttc caacaatc                            38

<210> SEQ ID NO 14
<211> LENGTH: 67
<212> TYPE: DNA
<213> ORGANISM: Artificial
<220> FEATURE:
<223> OTHER INFORMATION: Synthetic DNA

<400> SEQUENCE: 14
ccatttacta acattcgagg tgtacaagca caagttttgc aggctttcga aagaactgat    60
ttcgatc                                                              67

<210> SEQ ID NO 15
<211> LENGTH: 85
<212> TYPE: DNA
<213> ORGANISM: Artificial
<220> FEATURE:
<223> OTHER INFORMATION: Synthetic DNA

<400> SEQUENCE: 15
gaatgttagt aaatggatat cttttaaaac tcaaacaaa aatcagtgtt tgttatacat    60
gccaaagcct gcttagctct ttcac                                          85

<210> SEQ ID NO 16
<211> LENGTH: 37
<212> TYPE: DNA
<213> ORGANISM: Artificial
<220> FEATURE:
<223> OTHER INFORMATION: Synthetic DNA

<400> SEQUENCE: 16
caaggagaaa aaaccatgtc taacttgttg actgttc                             37

<210> SEQ ID NO 17
<211> LENGTH: 30
<212> TYPE: DNA
<213> ORGANISM: Artificial
```

```
<220> FEATURE:
<223> OTHER INFORMATION: Synthetic DNA

<400> SEQUENCE: 17 tggtttttc tccttgacgt taaagtatag                                        30

<210> SEQ ID NO 18
<211> LENGTH: 71
<212> TYPE: DNA
<213> ORGANISM: Artificial
<220> FEATURE:
<223> OTHER INFORMATION: Synthetic DNA

<400> SEQUENCE: 18
cagtcgtaga tgcgtaaaat accgttcgta taatgtatgc tatacgaagt tatacggatt     60
agaagccgcc g                                                          71

<210> SEQ ID NO 19
<211> LENGTH: 83
<212> TYPE: DNA
<213> ORGANISM: Artificial
<220> FEATURE:
<223> OTHER INFORMATION: Synthetic DNA

<400> SEQUENCE: 19
acgcatctac gactgtgggt cccgtggaga aatgtatgaa accctgtatg gagagtgatt     60
cagtcacgac gttgtaaaac gac                                             83

<210> SEQ ID NO 20
<211> LENGTH: 79
<212> TYPE: DNA
<213> ORGANISM: Artificial
<220> FEATURE:
<223> OTHER INFORMATION: Synthetic DNA

<400> SEQUENCE: 20
tggggacacc atcccgcctc aatcacaggg cgggaaataa gctacaatta acgccaaact     60
ctcagtacaa tctgctctg                                                  79

<210> SEQ ID NO 21
<211> LENGTH: 65
<212> TYPE: DNA
<213> ORGANISM: Artificial
<220> FEATURE:
<223> OTHER INFORMATION: Synthetic DNA

<400> SEQUENCE: 21
cgtggagaaa tgtatgaaac cctgtatgga gagtgattca gttccagcca gtaaaatcca     60
tactc                                                                 65

<210> SEQ ID NO 22
<211> LENGTH: 62
<212> TYPE: DNA
<213> ORGANISM: Artificial
<220> FEATURE:
<223> OTHER INFORMATION: Synthetic DNA

<400> SEQUENCE: 22
agtgcgtcgg cagtaccgga tcctaaagcc gattcaagaa aagtcttttt gccagccagt     60
cc                                                                    62

<210> SEQ ID NO 23
```

-continued

```
<211> LENGTH: 55
<212> TYPE: DNA
<213> ORGANISM: Artificial
<220> FEATURE:
<223> OTHER INFORMATION: Synthetic DNA

<400> SEQUENCE: 23
tactgccgac gcactttaga acggccaccg tcctcagtca cgacgttgta aaacg          55

<210> SEQ ID NO 24
<211> LENGTH: 59
<212> TYPE: DNA
<213> ORGANISM: Artificial
<220> FEATURE:
<223> OTHER INFORMATION: Synthetic DNA

<400> SEQUENCE: 24
atacatttct ccacgggacc cacagtcgta gatgcgtact ctcagtacaa tctgctctg      59

<210> SEQ ID NO 25
<211> LENGTH: 68
<212> TYPE: DNA
<213> ORGANISM: Artificial
<220> FEATURE:
<223> OTHER INFORMATION: Synthetic DNA

<400> SEQUENCE: 25
gtggcccggg agagacagtt tagtagtgac tcgcggccag ttggggctaa acgagatttg      60
gaatattg                                                              68

<210> SEQ ID NO 26
<211> LENGTH: 104
<212> TYPE: DNA
<213> ORGANISM: Artificial
<220> FEATURE:
<223> OTHER INFORMATION: Synthetic DNA

<400> SEQUENCE: 26
gccttcacat atagtataac ttcgtataat gtatgctata cgaacggtaa aaatctttaa      60
aaaatttcca attttccttt acgatttata ttacagtatt ttcc                      104

<210> SEQ ID NO 27
<211> LENGTH: 81
<212> TYPE: DNA
<213> ORGANISM: Artificial
<220> FEATURE:
<223> OTHER INFORMATION: Synthetic DNA

<400> SEQUENCE: 27
actatatgtg aaggcatggc tatggcacgg cagacattcc gccagatcat caataggcac      60
cagtcacgac gttgtaaaac g                                               81

<210> SEQ ID NO 28
<211> LENGTH: 60
<212> TYPE: DNA
<213> ORGANISM: Artificial
<220> FEATURE:
<223> OTHER INFORMATION: Synthetic DNA

<400> SEQUENCE: 28
tctctcccgg gccacgacgc taggccagta cctccactct cagtacaatc tgctctgatg      60

<210> SEQ ID NO 29
<211> LENGTH: 64
```

```
<212> TYPE: DNA
<213> ORGANISM: Artificial
<220> FEATURE:
<223> OTHER INFORMATION: Synthetic DNA

<400> SEQUENCE: 29
tggcacggca gacattccgc cagatcatca ataggcacca gtgtctcttg cagaacacaa      60
taag                                                                  64

<210> SEQ ID NO 30
<211> LENGTH: 48
<212> TYPE: DNA
<213> ORGANISM: Artificial
<220> FEATURE:
<223> OTHER INFORMATION: Synthetic DNA

<400> SEQUENCE: 30
gttgaatatg gctcatcctt gtattactcg tttgttctgt ttctattc                  48

<210> SEQ ID NO 31
<211> LENGTH: 23
<212> TYPE: DNA
<213> ORGANISM: Artificial
<220> FEATURE:
<223> OTHER INFORMATION: Synthetic DNA

<400> SEQUENCE: 31
atgagccata ttcaacggga aac                                             23

<210> SEQ ID NO 32
<211> LENGTH: 38
<212> TYPE: DNA
<213> ORGANISM: Artificial
<220> FEATURE:
<223> OTHER INFORMATION: Synthetic DNA

<400> SEQUENCE: 32
tttagtagac atgcattaca accaattaac caattctg                             38

<210> SEQ ID NO 33
<211> LENGTH: 37
<212> TYPE: DNA
<213> ORGANISM: Artificial
<220> FEATURE:
<223> OTHER INFORMATION: Synthetic DNA

<400> SEQUENCE: 33
tgcatgtcta ctaaactcac aaattagagc ttcaatt                              37

<210> SEQ ID NO 34
<211> LENGTH: 32
<212> TYPE: DNA
<213> ORGANISM: Artificial
<220> FEATURE:
<223> OTHER INFORMATION: Synthetic DNA

<400> SEQUENCE: 34
gggtaataac tgatataatt aaattgaagc tc                                   32

<210> SEQ ID NO 35
<211> LENGTH: 37
<212> TYPE: DNA
<213> ORGANISM: Artificial
<220> FEATURE:
<223> OTHER INFORMATION: Synthetic DNA
```

-continued

<400> SEQUENCE: 35
tatcagttat tacccagctt gcaaattaaa gccttcg                                    37

<210> SEQ ID NO 36
<211> LENGTH: 26
<212> TYPE: DNA
<213> ORGANISM: Artificial
<220> FEATURE:
<223> OTHER INFORMATION: Synthetic DNA

<400> SEQUENCE: 36
ttagttatgt cacgcttaca ttcacg                                              26

<210> SEQ ID NO 37
<211> LENGTH: 38
<212> TYPE: DNA
<213> ORGANISM: Artificial
<220> FEATURE:
<223> OTHER INFORMATION: Synthetic DNA

<400> SEQUENCE: 37
gcgtgacata actaatcaat caccatcttc caacaatc                                  38

<210> SEQ ID NO 38
<211> LENGTH: 67
<212> TYPE: DNA
<213> ORGANISM: Artificial
<220> FEATURE:
<223> OTHER INFORMATION: Synthetic DNA

<400> SEQUENCE: 38
ccatttacta acattcgagg tgtacaagca caagttttgc aggctttcga aagaactgat          60
ttcgatc                                                                   67

<210> SEQ ID NO 39
<211> LENGTH: 85
<212> TYPE: DNA
<213> ORGANISM: Artificial
<220> FEATURE:
<223> OTHER INFORMATION: Synthetic DNA

<400> SEQUENCE: 39
gaatgttagt aaatggatat cttttaaaac tcaaaacaaa aatcagtgtt tgttatacat          60
gccaaagcct gcttagctct ttcac                                               85

<210> SEQ ID NO 40
<211> LENGTH: 37
<212> TYPE: DNA
<213> ORGANISM: Artificial
<220> FEATURE:
<223> OTHER INFORMATION: Synthetic DNA

<400> SEQUENCE: 40
caaggagaaa aaaccatgtc taacttgttg actgttc                                   37

<210> SEQ ID NO 41
<211> LENGTH: 30
<212> TYPE: DNA
<213> ORGANISM: Artificial
<220> FEATURE:
<223> OTHER INFORMATION: Synthetic DNA

<400> SEQUENCE: 41 tggtttttc tccttgacgt taaagtatag                                           30

```
<210> SEQ ID NO 42
<211> LENGTH: 58
<212> TYPE: DNA
<213> ORGANISM: Artificial
<220> FEATURE:
<223> OTHER INFORMATION: Synthetic DNA

<400> SEQUENCE: 42
gaatcattta gacacgggca tcgtcctctc gaaaggtgaa aaacggatta gaagccgc          58

<210> SEQ ID NO 43
<211> LENGTH: 58
<212> TYPE: DNA
<213> ORGANISM: Artificial
<220> FEATURE:
<223> OTHER INFORMATION: Synthetic DNA

<400> SEQUENCE: 43
gtgtctaaat gattcgacca gcctaagaat gttcaaccag tcacgacgtt gtaaaacg          58

<210> SEQ ID NO 44
<211> LENGTH: 59
<212> TYPE: DNA
<213> ORGANISM: Artificial
<220> FEATURE:
<223> OTHER INFORMATION: Synthetic DNA

<400> SEQUENCE: 44
atgtctgccg tgccatagcc atgccttcac atatagtact ctcagtacaa tctgctctg          59

<210> SEQ ID NO 45
<211> LENGTH: 70
<212> TYPE: DNA
<213> ORGANISM: Artificial
<220> FEATURE:
<223> OTHER INFORMATION: Synthetic DNA

<400> SEQUENCE: 45
ctaagaatgt tcaacataac ttcgtatagc atacattata cgaacggtac agttccagcc          60
agtaaaatcc                                                               70

<210> SEQ ID NO 46
<211> LENGTH: 62
<212> TYPE: DNA
<213> ORGANISM: Artificial
<220> FEATURE:
<223> OTHER INFORMATION: Synthetic DNA

<400> SEQUENCE: 46
agtgcgtcgg cagtaccgga tcctaaagcc gattcaagaa aagtcttttt gccagccagt          60
cc                                                                       62

<210> SEQ ID NO 47
<211> LENGTH: 55
<212> TYPE: DNA
<213> ORGANISM: Artificial
<220> FEATURE:
<223> OTHER INFORMATION: Synthetic DNA

<400> SEQUENCE: 47
tactgccgac gcactttaga acggccaccg tcctcagtca cgacgttgta aaacg             55

<210> SEQ ID NO 48
```

```
<211> LENGTH: 80
<212> TYPE: DNA
<213> ORGANISM: Artificial
<220> FEATURE:
<223> OTHER INFORMATION: Synthetic DNA

<400> SEQUENCE: 48
gttgaacatt cttaggctgg tcgaatcatt tagacacggg catcgtcctc tcgaaaggtg       60
actctcagta caatctgctc                                                   80

<210> SEQ ID NO 49
<211> LENGTH: 60
<212> TYPE: DNA
<213> ORGANISM: Artificial
<220> FEATURE:
<223> OTHER INFORMATION: Synthetic DNA

<400> SEQUENCE: 49
atttcccgcc ctgtgattga ggcgggatgg tgtccccaca gtggtcatca ataagcctgg       60

<210> SEQ ID NO 50
<211> LENGTH: 77
<212> TYPE: DNA
<213> ORGANISM: Artificial
<220> FEATURE:
<223> OTHER INFORMATION: Synthetic DNA

<400> SEQUENCE: 50
gccttcacat atagtataac ttcgtataat gtatgctata cgaacggtaa aaagatattt       60
ccagtgctaa ggtcaac                                                      77

<210> SEQ ID NO 51
<211> LENGTH: 80
<212> TYPE: DNA
<213> ORGANISM: Artificial
<220> FEATURE:
<223> OTHER INFORMATION: Synthetic DNA

<400> SEQUENCE: 51
actatatgtg aaggcatggc tatggcacgg cagacattcc gccagatcat caataggcac       60
cagtcacgac gttgtaaaac                                                   80

<210> SEQ ID NO 52
<211> LENGTH: 54
<212> TYPE: DNA
<213> ORGANISM: Artificial
<220> FEATURE:
<223> OTHER INFORMATION: Synthetic DNA

<400> SEQUENCE: 52
cacagggcgg gaaataagct acaattaacg ccaaactctc agtacaatct gctc             54

<210> SEQ ID NO 53
<211> LENGTH: 71
<212> TYPE: DNA
<213> ORGANISM: Artificial
<220> FEATURE:
<223> OTHER INFORMATION: Synthetic DNA

<400> SEQUENCE: 53
ctaagaatgt tcaacataac ttcgtatagc atacattata cgaacggtac agttgtacca       60
acctgcattt c                                                            71
```

<210> SEQ ID NO 54
<211> LENGTH: 66
<212> TYPE: DNA
<213> ORGANISM: Artificial
<220> FEATURE:
<223> OTHER INFORMATION: Synthetic DNA

<400> SEQUENCE: 54
atacatttct ccacgggacc cacagtcgta gatgcgtaaa agctcacttg tttcttgatt     60
ttttag     66

<210> SEQ ID NO 55
<211> LENGTH: 59
<212> TYPE: DNA
<213> ORGANISM: Artificial
<220> FEATURE:
<223> OTHER INFORMATION: Synthetic DNA

<400> SEQUENCE: 55
cgtggagaaa tgtatgaaac cctgtatgga gagtgattca gtcacgacgt tgtaaaacg     59

<210> SEQ ID NO 56
<211> LENGTH: 82
<212> TYPE: DNA
<213> ORGANISM: Artificial
<220> FEATURE:
<223> OTHER INFORMATION: Synthetic DNA

<400> SEQUENCE: 56
gttgaacatt cttaggctgg tcgaatcatt tagacacggg catcgtcctc tcgaaaggtg     60
actctcagta caatctgctc tg     82

<210> SEQ ID NO 57
<211> LENGTH: 60
<212> TYPE: DNA
<213> ORGANISM: Artificial
<220> FEATURE:
<223> OTHER INFORMATION: Synthetic DNA

<400> SEQUENCE: 57
cgtggcccgg gagagacagt ttagtagtga ctcgcggcca gtatgagtcg ggcaattccg     60

<210> SEQ ID NO 58
<211> LENGTH: 77
<212> TYPE: DNA
<213> ORGANISM: Artificial
<220> FEATURE:
<223> OTHER INFORMATION: Synthetic DNA

<400> SEQUENCE: 58
caatcacagg gcgggaaata agctacaatt aacgccaaaa aatatcgtta atatttcgta     60
tgtgtattct ttgtaag     77

<210> SEQ ID NO 59
<211> LENGTH: 55
<212> TYPE: DNA
<213> ORGANISM: Artificial
<220> FEATURE:
<223> OTHER INFORMATION: Synthetic DNA

<400> SEQUENCE: 59
cccgccctgt gattgaggcg ggatggtgtc cccacagtca cgacgttgta aaacg     55

<210> SEQ ID NO 60

<211> LENGTH: 50
<212> TYPE: DNA
<213> ORGANISM: Artificial
<220> FEATURE:
<223> OTHER INFORMATION: Synthetic DNA

<400> SEQUENCE: 60
ctctcccggg ccacgacgct aggccagtac actctcagta caatctgctc            50

<210> SEQ ID NO 61
<211> LENGTH: 76
<212> TYPE: DNA
<213> ORGANISM: Artificial
<220> FEATURE:
<223> OTHER INFORMATION: Synthetic DNA

<400> SEQUENCE: 61
gggatggtgt ccccacagtt accgttcgta tagcatacat tatacgaagt tatgttactc            60
tcacactctt tagttc            76

<210> SEQ ID NO 62
<211> LENGTH: 50
<212> TYPE: DNA
<213> ORGANISM: Artificial
<220> FEATURE:
<223> OTHER INFORMATION: Synthetic DNA

<400> SEQUENCE: 62
tcaccgaaat cttcatattg atattgttcg ataattaaat ctttcttatc            50

<210> SEQ ID NO 63
<211> LENGTH: 22
<212> TYPE: DNA
<213> ORGANISM: Artificial
<220> FEATURE:
<223> OTHER INFORMATION: Synthetic DNA

<400> SEQUENCE: 63
atgaagattt cggtgatccc tg            22

<210> SEQ ID NO 64
<211> LENGTH: 20
<212> TYPE: DNA
<213> ORGANISM: Artificial
<220> FEATURE:
<223> OTHER INFORMATION: Synthetic DNA

<400> SEQUENCE: 64
ttaggcgtca tcctgtgctc            20

<210> SEQ ID NO 65
<211> LENGTH: 45
<212> TYPE: DNA
<213> ORGANISM: Artificial
<220> FEATURE:
<223> OTHER INFORMATION: Synthetic DNA

<400> SEQUENCE: 65
caggatgacg cctaaaaaga ttctcttttt ttatgatatt tgtac            45

<210> SEQ ID NO 66
<211> LENGTH: 30
<212> TYPE: DNA
<213> ORGANISM: Artificial
<220> FEATURE:
<223> OTHER INFORMATION: Synthetic DNA -continued

<400> SEQUENCE: 66
aggaatcata gtttcatgat tttctgttac                                          30

<210> SEQ ID NO 67
<211> LENGTH: 33
<212> TYPE: DNA
<213> ORGANISM: Artificial
<220> FEATURE:
<223> OTHER INFORMATION: Synthetic DNA

<400> SEQUENCE: 67
gaaactatga ttcctacgga ttagaagccg ccg                                      33

<210> SEQ ID NO 68
<211> LENGTH: 30
<212> TYPE: DNA
<213> ORGANISM: Artificial
<220> FEATURE:
<223> OTHER INFORMATION: Synthetic DNA

<400> SEQUENCE: 68
tggttttttc tccttgacgt taaagtatag                                          30

<210> SEQ ID NO 69
<211> LENGTH: 37
<212> TYPE: DNA
<213> ORGANISM: Artificial
<220> FEATURE:
<223> OTHER INFORMATION: Synthetic DNA

<400> SEQUENCE: 69
caaggagaaa aaaccatgtc taacttgttg actgttc                                  37

<210> SEQ ID NO 70
<211> LENGTH: 67
<212> TYPE: DNA
<213> ORGANISM: Artificial
<220> FEATURE:
<223> OTHER INFORMATION: Synthetic DNA

<400> SEQUENCE: 70
ccatttacta acattcgagg tgtacaagca caagttttgc aggctttcga aagaactgat         60
ttcgatc                                                                   67

<210> SEQ ID NO 71
<211> LENGTH: 36
<212> TYPE: DNA
<213> ORGANISM: Artificial
<220> FEATURE:
<223> OTHER INFORMATION: Synthetic DNA

<400> SEQUENCE: 71
gtttgttata catgccaaag cctgcttagc tctttc                                   36

<210> SEQ ID NO 72
<211> LENGTH: 37
<212> TYPE: DNA
<213> ORGANISM: Artificial
<220> FEATURE:
<223> OTHER INFORMATION: Synthetic DNA

<400> SEQUENCE: 72
caaggagaaa aaaccatgtc taacttgttg actgttc                                  37

-continued

<210> SEQ ID NO 73
<211> LENGTH: 30
<212> TYPE: DNA
<213> ORGANISM: Artificial
<220> FEATURE:
<223> OTHER INFORMATION: Synthetic DNA

<400> SEQUENCE: 73 tggtttttc tccttgacgt taaagtatag                                          30

<210> SEQ ID NO 74
<211> LENGTH: 45
<212> TYPE: DNA
<213> ORGANISM: Artificial
<220> FEATURE:
<223> OTHER INFORMATION: Synthetic DNA

<400> SEQUENCE: 74
cagtcgtaga tgcgtaaaat accgttcgta taatgtatgc tatac                        45

<210> SEQ ID NO 75
<211> LENGTH: 83
<212> TYPE: DNA
<213> ORGANISM: Artificial
<220> FEATURE:
<223> OTHER INFORMATION: Synthetic DNA

<400> SEQUENCE: 75
acgcatctac gactgtgggt cccgtggaga aatgtatgaa accctgtatg gagagtgatt        60
cagtcacgac gttgtaaaac gac                                                83

<210> SEQ ID NO 76
<211> LENGTH: 79
<212> TYPE: DNA
<213> ORGANISM: Artificial
<220> FEATURE:
<223> OTHER INFORMATION: Synthetic DNA

<400> SEQUENCE: 76
tggggacacc atcccgcctc aatcacaggg cgggaaataa gctacaatta acgccaaact        60
ctcagtacaa tctgctctg                                                     79

<210> SEQ ID NO 77
<211> LENGTH: 61
<212> TYPE: DNA
<213> ORGANISM: Artificial
<220> FEATURE:
<223> OTHER INFORMATION: Synthetic DNA

<400> SEQUENCE: 77
cgtggagaaa tgtatgaaac cctgtatgga gagtgattca gtattcatac atacccgtat        60
g                                                                        61

<210> SEQ ID NO 78
<211> LENGTH: 61
<212> TYPE: DNA
<213> ORGANISM: Artificial
<220> FEATURE:
<223> OTHER INFORMATION: Synthetic DNA

<400> SEQUENCE: 78
agtgcgtcgg cagtaccgga tcctaaagcc gattcaagaa aatgaccgga tgaaaccacc        60
g                                                                        61

<210> SEQ ID NO 79
<211> LENGTH: 55
<212> TYPE: DNA
<213> ORGANISM: Artificial
<220> FEATURE:
<223> OTHER INFORMATION: Synthetic DNA

<400> SEQUENCE: 79
tactgccgac gcactttaga acggccaccg tcctcagtca cgacgttgta aaacg          55

<210> SEQ ID NO 80
<211> LENGTH: 59
<212> TYPE: DNA
<213> ORGANISM: Artificial
<220> FEATURE:
<223> OTHER INFORMATION: Synthetic DNA

<400> SEQUENCE: 80
atacatttct ccacgggacc cacagtcgta gatgcgtact ctcagtacaa tctgctctg          59

<210> SEQ ID NO 81
<211> LENGTH: 60
<212> TYPE: DNA
<213> ORGANISM: Artificial
<220> FEATURE:
<223> OTHER INFORMATION: Synthetic DNA

<400> SEQUENCE: 81
cgtggcccgg gagagacagt ttagtagtga ctcgcggcca gtatgagtcg ggcaattccg          60

<210> SEQ ID NO 82
<211> LENGTH: 93
<212> TYPE: DNA
<213> ORGANISM: Artificial
<220> FEATURE:
<223> OTHER INFORMATION: Synthetic DNA

<400> SEQUENCE: 82
gccttcacat atagtataac ttcgtataat gtatgctata cgaacggtaa aaatatcgtt          60
aatatttcgt atgtgtattc tttgtaagca atg          93

<210> SEQ ID NO 83
<211> LENGTH: 80
<212> TYPE: DNA
<213> ORGANISM: Artificial
<220> FEATURE:
<223> OTHER INFORMATION: Synthetic DNA

<400> SEQUENCE: 83
actatatgtg aaggcatggc tatggcacgg cagacattcc gccagatcat caataggcac          60
cagtcacgac gttgtaaaac          80

<210> SEQ ID NO 84
<211> LENGTH: 60
<212> TYPE: DNA
<213> ORGANISM: Artificial
<220> FEATURE:
<223> OTHER INFORMATION: Synthetic DNA

<400> SEQUENCE: 84
tctctcccgg gccacgacgc taggccagta cctccactct cagtacaatc tgctctgatg          60

<210> SEQ ID NO 85

-continued

```
<211> LENGTH: 35
<212> TYPE: DNA
<213> ORGANISM: Artificial
<220> FEATURE:
<223> OTHER INFORMATION: Synthetic DNA

<400> SEQUENCE: 85
tggcacggca gacattccgc cagatcatca atagg                            35

<210> SEQ ID NO 86
<211> LENGTH: 50
<212> TYPE: DNA
<213> ORGANISM: Artificial
<220> FEATURE:
<223> OTHER INFORMATION: Synthetic DNA

<400> SEQUENCE: 86
tcaccgaaat cttcatattg atattgttcg ataattaaat ctttcttatc           50

<210> SEQ ID NO 87
<211> LENGTH: 22
<212> TYPE: DNA
<213> ORGANISM: Artificial
<220> FEATURE:
<223> OTHER INFORMATION: Synthetic DNA

<400> SEQUENCE: 87
atgaagattt cggtgatccc tg                                          22

<210> SEQ ID NO 88
<211> LENGTH: 20
<212> TYPE: DNA
<213> ORGANISM: Artificial
<220> FEATURE:
<223> OTHER INFORMATION: Synthetic DNA

<400> SEQUENCE: 88
ttaggcgtca tcctgtgctc                                             20

<210> SEQ ID NO 89
<211> LENGTH: 45
<212> TYPE: DNA
<213> ORGANISM: Artificial
<220> FEATURE:
<223> OTHER INFORMATION: Synthetic DNA

<400> SEQUENCE: 89
caggatgacg cctaaaaaga ttctcttttt ttatgatatt tgtac                45

<210> SEQ ID NO 90
<211> LENGTH: 30
<212> TYPE: DNA
<213> ORGANISM: Artificial
<220> FEATURE:
<223> OTHER INFORMATION: Synthetic DNA

<400> SEQUENCE: 90
aggaatcata gtttcatgat tttctgttac                                 30

<210> SEQ ID NO 91
<211> LENGTH: 33
<212> TYPE: DNA
<213> ORGANISM: Artificial
<220> FEATURE:
<223> OTHER INFORMATION: Synthetic DNA

<400> SEQUENCE: 91
```
gaaactatga ttcctacgga ttagaagccg ccg                                      33

<210> SEQ ID NO 92
<211> LENGTH: 30
<212> TYPE: DNA
<213> ORGANISM: Artificial
<220> FEATURE:
<223> OTHER INFORMATION: Synthetic DNA

<400> SEQUENCE: 92
tggttttttc tccttgacgt taaagtatag                                          30

<210> SEQ ID NO 93
<211> LENGTH: 37
<212> TYPE: DNA
<213> ORGANISM: Artificial
<220> FEATURE:
<223> OTHER INFORMATION: Synthetic DNA

<400> SEQUENCE: 93
caaggagaaa aaaccatgtc taacttgttg actgttc                                  37

<210> SEQ ID NO 94
<211> LENGTH: 85
<212> TYPE: DNA
<213> ORGANISM: Artificial
<220> FEATURE:
<223> OTHER INFORMATION: Synthetic DNA

<400> SEQUENCE: 94
gaatgttagt aaatggatat cttttaaaac tcaaacaaa aatcagtgtt tgttatacat          60
gccaaagcct gcttagctct ttcac                                               85

<210> SEQ ID NO 95
<211> LENGTH: 67
<212> TYPE: DNA
<213> ORGANISM: Artificial
<220> FEATURE:
<223> OTHER INFORMATION: Synthetic DNA

<400> SEQUENCE: 95
ccatttacta acattcgagg tgtacaagca caagttttgc aggctttcga aagaactgat         60
ttcgatc                                                                   67

<210> SEQ ID NO 96
<211> LENGTH: 38
<212> TYPE: DNA
<213> ORGANISM: Artificial
<220> FEATURE:
<223> OTHER INFORMATION: Synthetic DNA

<400> SEQUENCE: 96
gcgtgacata actaatcaat caccatcttc caacaatc                                 38

<210> SEQ ID NO 97
<211> LENGTH: 26
<212> TYPE: DNA
<213> ORGANISM: Artificial
<220> FEATURE:
<223> OTHER INFORMATION: Synthetic DNA

<400> SEQUENCE: 97
ttagttatgt cacgcttaca ttcacg                                              26

<210> SEQ ID NO 98
<211> LENGTH: 64
<212> TYPE: DNA
<213> ORGANISM: Artificial
<220> FEATURE:
<223> OTHER INFORMATION: Synthetic DNA

<400> SEQUENCE: 98
gaatcattta gacacgggca tcgtcctctc gaaaggtgaa aaagcttgca aattaaagcc      60
ttcg                                                                   64

<210> SEQ ID NO 99
<211> LENGTH: 58
<212> TYPE: DNA
<213> ORGANISM: Artificial
<220> FEATURE:
<223> OTHER INFORMATION: Synthetic DNA

<400> SEQUENCE: 99
gtgtctaaat gattcgacca gcctaagaat gttcaaccag tcacgacgtt gtaaaacg       58

<210> SEQ ID NO 100
<211> LENGTH: 59
<212> TYPE: DNA
<213> ORGANISM: Artificial
<220> FEATURE:
<223> OTHER INFORMATION: Synthetic DNA

<400> SEQUENCE: 100
atgtctgccg tgccatagcc atgccttcac atatagtact ctcagtacaa tctgctctg      59

<210> SEQ ID NO 101
<211> LENGTH: 42
<212> TYPE: DNA
<213> ORGANISM: Artificial
<220> FEATURE:
<223> OTHER INFORMATION: Synthetic DNA

<400> SEQUENCE: 101
ctaagaatgt tcaacataac ttcgtatagc atacattata cg                        42

<210> SEQ ID NO 102
<211> LENGTH: 61
<212> TYPE: DNA
<213> ORGANISM: Artificial
<220> FEATURE:
<223> OTHER INFORMATION: Synthetic DNA

<400> SEQUENCE: 102
agtgcgtcgg cagtaccgga tcctaaagcc gattcaagaa aatgaccgga tgaaaccacc      60
g                                                                      61

<210> SEQ ID NO 103
<211> LENGTH: 55
<212> TYPE: DNA
<213> ORGANISM: Artificial
<220> FEATURE:
<223> OTHER INFORMATION: Synthetic DNA

<400> SEQUENCE: 103
tactgccgac gcactttaga acggccaccg tcctcagtca cgacgttgta aaacg          55

<210> SEQ ID NO 104
<211> LENGTH: 80

-continued

```
<212> TYPE: DNA
<213> ORGANISM: Artificial
<220> FEATURE:
<223> OTHER INFORMATION: Synthetic DNA

<400> SEQUENCE: 104
gttgaacatt cttaggctgg tcgaatcatt tagacacggg catcgtcctc tcgaaaggtg     60
actctcagta caatctgctc                                                  80

<210> SEQ ID NO 105
<211> LENGTH: 44
<212> TYPE: DNA
<213> ORGANISM: Artificial
<220> FEATURE:
<223> OTHER INFORMATION: Synthetic DNA

<400> SEQUENCE: 105
gggatggtgt ccccacagtt gtccagacta cgtcgaatcc ttac                       44

<210> SEQ ID NO 106
<211> LENGTH: 73
<212> TYPE: DNA
<213> ORGANISM: Artificial
<220> FEATURE:
<223> OTHER INFORMATION: Synthetic DNA

<400> SEQUENCE: 106
gccttcacat atagtataac ttcgtataat gtatgctata cgaacggtaa aaattttggc     60
caaatgccac agc                                                         73

<210> SEQ ID NO 107
<211> LENGTH: 81
<212> TYPE: DNA
<213> ORGANISM: Artificial
<220> FEATURE:
<223> OTHER INFORMATION: Synthetic DNA

<400> SEQUENCE: 107
actatatgtg aaggcatggc tatggcacgg cagacattcc gccagatcat caataggcac     60
cagtcacgac gttgtaaaac g                                                81

<210> SEQ ID NO 108
<211> LENGTH: 79
<212> TYPE: DNA
<213> ORGANISM: Artificial
<220> FEATURE:
<223> OTHER INFORMATION: Synthetic DNA

<400> SEQUENCE: 108
tggggacacc atcccgcctc aatcacaggg cgggaaataa gctacaatta acgccaaact     60
ctcagtacaa tctgctctg                                                   79

<210> SEQ ID NO 109
<211> LENGTH: 71
<212> TYPE: DNA
<213> ORGANISM: Artificial
<220> FEATURE:
<223> OTHER INFORMATION: Synthetic DNA

<400> SEQUENCE: 109
ctaagaatgt tcaacataac ttcgtatagc atacattata cgaacggtac agtagtgaag     60
gcgtcatcct c                                                           71
```

<210> SEQ ID NO 110
<211> LENGTH: 39
<212> TYPE: DNA
<213> ORGANISM: Artificial
<220> FEATURE:
<223> OTHER INFORMATION: Synthetic DNA

<400> SEQUENCE: 110
cagtcgtaga tgcgtaaaat cgaaagaagg ccgcatgac                         39

<210> SEQ ID NO 111
<211> LENGTH: 83
<212> TYPE: DNA
<213> ORGANISM: Artificial
<220> FEATURE:
<223> OTHER INFORMATION: Synthetic DNA

<400> SEQUENCE: 111
acgcatctac gactgtgggt cccgtggaga aatgtatgaa accctgtatg gagagtgatt   60
cagtcacgac gttgtaaaac gac                                          83

<210> SEQ ID NO 112
<211> LENGTH: 82
<212> TYPE: DNA
<213> ORGANISM: Artificial
<220> FEATURE:
<223> OTHER INFORMATION: Synthetic DNA

<400> SEQUENCE: 112
gttgaacatt cttaggctgg tcgaatcatt tagacacggg catcgtcctc tcgaaaggtg   60
actctcagta caatctgctc tg                                           82

<210> SEQ ID NO 113
<211> LENGTH: 20
<212> TYPE: DNA
<213> ORGANISM: Artificial
<220> FEATURE:
<223> OTHER INFORMATION: Synthetic DNA

<400> SEQUENCE: 113
tggggctaaa cgagatttgg                                              20

<210> SEQ ID NO 114
<211> LENGTH: 17
<212> TYPE: DNA
<213> ORGANISM: Artificial
<220> FEATURE:
<223> OTHER INFORMATION: Synthetic DNA

<400> SEQUENCE: 114
tggggacacc atcccgc                                                 17

<210> SEQ ID NO 115
<211> LENGTH: 26
<212> TYPE: DNA
<213> ORGANISM: Artificial
<220> FEATURE:
<223> OTHER INFORMATION: Synthetic DNA

<400> SEQUENCE: 115
ttggcgttaa ttgtagctta tttccc                                       26

<210> SEQ ID NO 116
<211> LENGTH: 35

```
<212> TYPE: DNA
<213> ORGANISM: Artificial
<220> FEATURE:
<223> OTHER INFORMATION: Synthetic DNA

<400> SEQUENCE: 116
aatcactctc catacagggt ttcatacatt tctcc                                   35

<210> SEQ ID NO 117
<211> LENGTH: 22
<212> TYPE: DNA
<213> ORGANISM: Artificial
<220> FEATURE:
<223> OTHER INFORMATION: Synthetic DNA

<400> SEQUENCE: 117
acgcatctac gactgtgggt cc                                                  22

<210> SEQ ID NO 118
<211> LENGTH: 20
<212> TYPE: DNA
<213> ORGANISM: Artificial
<220> FEATURE:
<223> OTHER INFORMATION: Synthetic DNA

<400> SEQUENCE: 118 gtcttttttgc cagccagtcc                                                   20

<210> SEQ ID NO 119
<211> LENGTH: 20
<212> TYPE: DNA
<213> ORGANISM: Artificial
<220> FEATURE:
<223> OTHER INFORMATION: Synthetic DNA

<400> SEQUENCE: 119
tggggctaaa cgagatttgg                                                    20

<210> SEQ ID NO 120
<211> LENGTH: 30
<212> TYPE: DNA
<213> ORGANISM: Artificial
<220> FEATURE:
<223> OTHER INFORMATION: Synthetic DNA

<400> SEQUENCE: 120
gtgcctattg atgatctggc ggaatgtctg                                         30

<210> SEQ ID NO 121
<211> LENGTH: 29
<212> TYPE: DNA
<213> ORGANISM: Artificial
<220> FEATURE:
<223> OTHER INFORMATION: Synthetic DNA

<400> SEQUENCE: 121
actatatgtg aaggcatggc tatggcacg                                          29

<210> SEQ ID NO 122
<211> LENGTH: 35
<212> TYPE: DNA
<213> ORGANISM: Artificial
<220> FEATURE:
<223> OTHER INFORMATION: Synthetic DNA

<400> SEQUENCE: 122
```

-continued gttgaacatt cttaggctgg tcgaatcatt tagac                                    35

<210> SEQ ID NO 123
<211> LENGTH: 24
<212> TYPE: DNA
<213> ORGANISM: Artificial
<220> FEATURE:
<223> OTHER INFORMATION: Synthetic DNA

<400> SEQUENCE: 123
cacctttcga gaggacgatg cccg                                                24

<210> SEQ ID NO 124
<211> LENGTH: 20
<212> TYPE: DNA
<213> ORGANISM: Artificial
<220> FEATURE:
<223> OTHER INFORMATION: Synthetic DNA

<400> SEQUENCE: 124 gtcttttgc cagccagtcc                                                      20

<210> SEQ ID NO 125
<211> LENGTH: 26
<212> TYPE: DNA
<213> ORGANISM: Artificial
<220> FEATURE:
<223> OTHER INFORMATION: Synthetic DNA

<400> SEQUENCE: 125
ttggcgttaa ttgtagctta tttccc                                              26

<210> SEQ ID NO 126
<211> LENGTH: 30
<212> TYPE: DNA
<213> ORGANISM: Artificial
<220> FEATURE:
<223> OTHER INFORMATION: Synthetic DNA

<400> SEQUENCE: 126
gtgcctattg atgatctggc ggaatgtctg                                          30

<210> SEQ ID NO 127
<211> LENGTH: 24
<212> TYPE: DNA
<213> ORGANISM: Artificial
<220> FEATURE:
<223> OTHER INFORMATION: Synthetic DNA

<400> SEQUENCE: 127
cacctttcga gaggacgatg cccg                                                24

<210> SEQ ID NO 128
<211> LENGTH: 35
<212> TYPE: DNA
<213> ORGANISM: Artificial
<220> FEATURE:
<223> OTHER INFORMATION: Synthetic DNA

<400> SEQUENCE: 128
aatcactctc catacagggt ttcatacatt tctcc                                    35

<210> SEQ ID NO 129
<211> LENGTH: 18
<212> TYPE: DNA
<213> ORGANISM: Artificial

-continued

<220> FEATURE:
<223> OTHER INFORMATION: Synthetic DNA

<400> SEQUENCE: 129
atgagtcggg caattccg                                                              18

<210> SEQ ID NO 130
<211> LENGTH: 17
<212> TYPE: DNA
<213> ORGANISM: Artificial
<220> FEATURE:
<223> OTHER INFORMATION: Synthetic DNA

<400> SEQUENCE: 130
tggggacacc atcccgc                                                               17

<210> SEQ ID NO 131
<211> LENGTH: 26
<212> TYPE: DNA
<213> ORGANISM: Artificial
<220> FEATURE:
<223> OTHER INFORMATION: Synthetic DNA

<400> SEQUENCE: 131
ttggcgttaa ttgtagctta tttccc                                                     26

<210> SEQ ID NO 132
<211> LENGTH: 35
<212> TYPE: DNA
<213> ORGANISM: Artificial
<220> FEATURE:
<223> OTHER INFORMATION: Synthetic DNA

<400> SEQUENCE: 132
aatcactctc catacagggt ttcatacatt tctcc                                           35

<210> SEQ ID NO 133
<211> LENGTH: 22
<212> TYPE: DNA
<213> ORGANISM: Artificial
<220> FEATURE:
<223> OTHER INFORMATION: Synthetic DNA

<400> SEQUENCE: 133
acgcatctac gactgtgggt cc                                                         22

<210> SEQ ID NO 134
<211> LENGTH: 18
<212> TYPE: DNA
<213> ORGANISM: Artificial
<220> FEATURE:
<223> OTHER INFORMATION: Synthetic DNA

<400> SEQUENCE: 134
tgaccggatg aaaccacc                                                              18

<210> SEQ ID NO 135
<211> LENGTH: 18
<212> TYPE: DNA
<213> ORGANISM: Artificial
<220> FEATURE:
<223> OTHER INFORMATION: Synthetic DNA

<400> SEQUENCE: 135
atgagtcggg caattccg                                                              18

```
<210> SEQ ID NO 136
<211> LENGTH: 30
<212> TYPE: DNA
<213> ORGANISM: Artificial
<220> FEATURE:
<223> OTHER INFORMATION: Synthetic DNA

<400> SEQUENCE: 136
gtgcctattg atgatctggc ggaatgtctg                                  30

<210> SEQ ID NO 137
<211> LENGTH: 29
<212> TYPE: DNA
<213> ORGANISM: Artificial
<220> FEATURE:
<223> OTHER INFORMATION: Synthetic DNA

<400> SEQUENCE: 137
actatatgtg aaggcatggc tatggcacg                                   29

<210> SEQ ID NO 138
<211> LENGTH: 35
<212> TYPE: DNA
<213> ORGANISM: Artificial
<220> FEATURE:
<223> OTHER INFORMATION: Synthetic DNA

<400> SEQUENCE: 138
gttgaacatt cttaggctgg tcgaatcatt tagac                            35

<210> SEQ ID NO 139
<211> LENGTH: 24
<212> TYPE: DNA
<213> ORGANISM: Artificial
<220> FEATURE:
<223> OTHER INFORMATION: Synthetic DNA

<400> SEQUENCE: 139
cacctttcga gaggacgatg cccg                                        24

<210> SEQ ID NO 140
<211> LENGTH: 18
<212> TYPE: DNA
<213> ORGANISM: Artificial
<220> FEATURE:
<223> OTHER INFORMATION: Synthetic DNA

<400> SEQUENCE: 140
tgaccggatg aaaccacc                                               18

<210> SEQ ID NO 141
<211> LENGTH: 26
<212> TYPE: DNA
<213> ORGANISM: Artificial
<220> FEATURE:
<223> OTHER INFORMATION: Synthetic DNA

<400> SEQUENCE: 141
ttggcgttaa ttgtagctta tttccc                                      26

<210> SEQ ID NO 142
<211> LENGTH: 30
<212> TYPE: DNA
<213> ORGANISM: Artificial
<220> FEATURE:
<223> OTHER INFORMATION: Synthetic DNA
```

-continued

```
<400> SEQUENCE: 142
gtgcctattg atgatctggc ggaatgtctg                                    30

<210> SEQ ID NO 143
<211> LENGTH: 24
<212> TYPE: DNA
<213> ORGANISM: Artificial
<220> FEATURE:
<223> OTHER INFORMATION: Synthetic DNA

<400> SEQUENCE: 143
cacctttcga gaggacgatg cccg                                          24

<210> SEQ ID NO 144
<211> LENGTH: 35
<212> TYPE: DNA
<213> ORGANISM: Artificial
<220> FEATURE:
<223> OTHER INFORMATION: Synthetic DNA

<400> SEQUENCE: 144
aatcactctc catacagggt ttcatacatt tctcc                              35
```

METHOD FOR PRODUCING TRANSFORMANT

CROSS REFERENCE TO RELATED APPLICATIONS

The present application claims priority from Japanese patent application JP 2020-200752 filed on Dec. 3, 2020, the content of which is hereby incorporated by reference into this application.

BACKGROUND

Technical Field

The present disclosure relates to a method for producing a transformant comprising deleting a particular region from a host genome with the use of a site-specific recombinase and a recognition sequence thereof.

Background Art

A site-specific recombinase is an enzyme that has activity of recognizing a particular, short, homologous pair of nucleotide sequences and causing homologous recombination between the pair of nucleotide sequences. When homologous recombination takes place between a pair of homologous nucleotide sequences aligned in the same direction, a region flanked by such pair of nucleotide sequences would be cleaved. When homologous recombination takes place between a pair of homologous nucleotide sequences aligned in the opposite direction, in contrast, a region flanked by such pair of nucleotide sequences would be inverted.

A site-specific recombinase and a recognition sequence thereof may be used to delete (knock out) a particular region from the host genome, or a selection marker gene may be located between a pair of nucleotide sequences to remove the selection marker gene. According to a technique involving the use of a site-specific recombinase and a recognition sequence thereof, a transformant or a gene recombinant that has traits different from the original traits can be produced. By efficiently producing a transformant or a gene recombinant with the utilization of such technique, for example, synthetic biology-based microbial metabolic engineering can be advanced and efficiency thereof can be promoted. Synthetic biology is a technique that is achieved by rapidly advancing a cycle of design, construction, evaluation, and learning of a production host. In synthetic biology involving the use of a yeast host, in particular, efficient host construction; i.e., efficient preparation of a recombinant yeast, is critical.

Transformation techniques involving the use of the yeast hosts can be roughly classified into a method involving the use of a cyclic plasmid comprising a target gene integrated therein and a method involving the use of a linear vector comprising a target gene. A target gene can be easily introduced into a yeast host using a cyclic plasmid, and a transgenic yeast can be prepared with high efficiency of approximately $10^{-2}$ (Gietz, R. D., et al., "High-efficiency yeast transformation using the LiAc/SS carrier DNA/PEG method," Nature Protocols, 2, 2007: 31-34). When a target gene is introduced into a yeast host using a linear vector, in contrast, it is necessary that the target gene be integrated into the genome via homologous recombination. Thus, efficiency for preparing a transgenic yeast would be approximately $10^{-6}$ at most (Storici, F, et al., "Chromosomal site-specific double-strand breaks are efficiently targeted for repair by oligonucleotides in yeast," Proc. Natl. Acad. Sci., U.S.A., 100, 2003: 14994-14999).

When a target gene is to be integrated into a particular site of genome DNA, the target gene is integrated into a site between a pair of homologous recombination sequences that enable homologous recombination with an upstream region and a downstream region of the site. As shown in FIG. 15, a nucleic acid fragment 100 containing an upstream region of the site, a nucleic acid fragment 101 containing a target gene, and a nucleic acid fragment 102 containing a downstream region of the site are introduced simultaneously, so that the target gene can be integrated into the particular site. In this case, homologous recombination regions are provided at the end of the nucleic acid fragment 100 containing the upstream region and at the end of the nucleic acid fragment 101 containing the target gene, so that the nucleic acid fragment 100 can be linked to the nucleic acid fragment 101 via homologous recombination. Also, homologous recombination regions are provided at the end of the nucleic acid fragment 101 and at the end of the nucleic acid fragment 102.

Because of the construction as shown in FIG. 15, the nucleic acid fragment 101 containing a target gene can be used in common, regardless of the site of the genome DNA into which such fragment is to be integrated. That is, the nucleic acid fragment 100 and the nucleic acid fragment 102 may be designed in accordance with the sites of the genome DNA into which the fragments are to be integrated. Thus, the nucleic acid fragment 101 containing a target gene can be used in common.

With the use of the site-specific recombinase and a recognition sequence thereof, a target gene included in the nucleic acid fragment 101 can be cleaved from genome DNA (not shown). When a selection marker gene is designated as a target gene, for example, a nucleic acid fragment may be first introduced, and a selection marker gene may then be removed (i.e., a marker recycle method).

SUMMARY

When a plurality of nucleic acid fragments including a nucleic acid fragment having a target gene are introduced into a host, however, a complicated step, such as a nucleic acid amplification reaction, was necessary to determine whether or not the plurality of nucleic acid fragments had been integrated into genome DNA as designed or the target gene had been accurately cleaved. Under the above circumstances, the present disclosure provides a method for producing a transformant that enables evaluation as to accurate integration of a plurality of nucleic acid fragments including a nucleic acid fragment having a target gene into the host genome DNA or accurate cleaving of a target gene in a simple manner, so that a transformant can be efficiently produced.

The present disclosure encompasses the following.

(1) A method for producing a transformant comprising steps of:

introducing a group of nucleic acid fragments comprising a nucleic acid fragment having a target gene, a nucleic acid fragment having either one of the pair of homologous recombination sequences corresponding to a particular region of genome DNA, and a nucleic acid fragment having the other of the pair of homologous recombination sequences into a host cell; and selecting a host cell in which the target gene flanked by the pair of recognition sequences recognized by a site-specific recombinase had been cleaved from genome DNA, wherein nucleic acid fragments constituting the group of nucleic acid fragments can be linked to each other via a homologous recombination sequence provided at the end of each nucleic acid fragment, and wherein at least one of the pair of recognition sequences is provided in a nucleic acid fragment other than the nucleic acid fragment having a target gene among the group of nucleic acid fragments.

(2) The method for producing a transformant according to (1), wherein the transformant lacks the particular region of genome DNA upon integration of nucleic acid fragments constituting the group of nucleic acid fragments therein.

(3) The method for producing a transformant according to (1), wherein the target gene is a selection marker gene.

(4) The method for producing a transformant according to (1) further comprising steps of:

introducing a group of nucleic acid fragments comprising a nucleic acid fragment having a target gene, a nucleic acid fragment having either one of the pair of homologous recombination sequences corresponding to the other region of genome DNA, and a nucleic acid fragment having the other of the pair of homologous recombination sequences into the selected host cell; and selecting a host cell in which the target gene flanked by the pair of recognition sequences recognized by a site-specific recombinase had been cleaved from genome DNA, wherein the nucleic acid fragment having the target gene introduced in the above step has the same homologous recombination sequence as the homologous recombination sequence in the nucleic acid fragment having a target gene introduced into the host cell in the previous step.

Advantageous Effects

In the method for producing a transformant according to the present disclosure, at least one recognition sequence of a pair of recognition sequences recognized by a site-specific recombinase is provided in a nucleic acid fragment other than a nucleic acid fragment having a target gene. In the case that a group of nucleic acid fragments are not accurately integrated into genome DNA, accordingly, it is not possible to cleave the target gene from genome DNA by the method of the present disclosure. According to the method for producing a transformant according to the present disclosure, whether or not a group of nucleic acid fragments were accurately integrated into genome DNA can be determined based on the target gene expression. As descried above, whether or not a group of nucleic acid fragments were accurately integrated into genome DNA can be determined in a very simple manner according to the method for producing a transformant of the present disclosure. Thus, a transformant can be produced in a very efficient manner.

BRIEF DESCRIPTION OF THE DRAWINGS

FIG. 1 is a configuration diagram that schematically shows a mechanism of integrating a target gene into the genome by the method for producing a transformant according to the present disclosure.

FIG. 2 is a configuration diagram that schematically shows a condition in which the target gene integrated by the method for producing a transformant according to the present disclosure is removed.

FIG. 3 is a configuration diagram that schematically shows a condition in which a group of nucleic acid fragments having target genes were erroneously integrated into the genome by the method for producing a transformant according to the present disclosure.

FIG. 4 is a configuration diagram that schematically shows a mechanism of integrating a target gene into the genome by a control method for producing a transformant and a condition in which the target gene is removed.

FIG. 5 is a configuration diagram that schematically shows a condition in which the target gene integrated by the control method for producing a transformant is removed and a nucleic acid fragment having a target gene is then integrated into the genome again.

FIG. 6 is a configuration diagram that schematically shows a mechanism of integrating a target gene into the genome by another embodiment of the method for producing a transformant according to the present disclosure.

FIG. 7 is a configuration diagram that schematically shows a condition in which the target gene integrated by the method for producing a transformant according to the present disclosure shown in FIG. 6 is removed.

FIG. 8 is a configuration diagram that schematically shows a GRE3-destructive linear vector set, which is prepared in the example, in which loxP is located in the same DNA fragment as the DNA fragment comprising a marker.

FIG. 9 is a configuration diagram that schematically shows a GRE3-destructive linear vector set, which is prepared in the example, in which loxP is located in a DNA fragment different from the DNA fragment comprising a marker.

FIG. 10 is a configuration diagram that schematically shows a GRE3-destructive linear vector set (5 fragments), which is prepared in the example, in which loxP is located in a DNA fragment different from the DNA fragment comprising a marker.

FIG. 11 is a configuration diagram that schematically shows an ADE1-destructive linear vector set, which is prepared in the example, in which loxP is located in the same DNA fragment as the DNA fragment comprising a marker.

FIG. 12 is a configuration diagram that schematically shows an ADE1-destructive linear vector set, which is prepared in the example, in which loxP is located in a DNA fragment different from the DNA fragment comprising a marker.

FIG. 13 is a configuration diagram that schematically shows an ADE1-destructive linear DNA fragment set (5 fragments), which is prepared in the example, in which loxP is located in a DNA fragment different from the DNA fragment comprising a marker.

FIG. 14 is a configuration diagram that schematically shows a condition in which homologous recombination had occurred between homologous sequences remaining in the first GRE3 locus and 3 DNA fragments when an ADE1-destructive linear DNA fragment set (5 fragments), which is prepared in the example, in which loxP is located in a DNA fragment different from the DNA fragment comprising a marker is used.

FIG. 15 is a configuration diagram that shows a scheme for integrating a target gene into a particular site of the genome DNA via homologous recombination using 3 nucleic acid fragments.

DETAILED DESCRIPTION

Hereafter, the present disclosure is described in greater detail with reference to the drawings and the examples.

In the method for producing a transformant according to the present disclosure (hereafter, referred to as "the method of the present disclosure"), a group of nucleic acid fragments comprising a target genes (i.e. a group of nucleic acid fragments comprising a nucleic acid fragment comprising the target gene and other nucleic acid fragments) are introduced into a particular position of the host genome DNA, so that a particular region is deleted from the genome DNA or a target gene is integrated into a particular position of the genome DNA, and genetic properties of the host are altered as a consequence. According to the method of the present disclosure, specifically, expression of the integrated target gene and deletion of a particular region from the genome DNA or expression of the integrated target gene would alter the genetic properties of the host.

A group of nucleic acid fragments is composed of a plurality of nucleic acid fragments. At least one nucleic acid fragment of a group of nucleic acid fragments comprises a target gene. A plurality of nucleic acid fragments constituting a group of nucleic acid fragments each have homologous sequences at both ends, so that the fragments can be integrated into the genome DNA or can be linked to each other via homologous recombination. Nucleic acid fragments located at the both ends when such plurality of nucleic acid fragments are linked to each other via homologous recombination have homologous sequences at the ends so as to integrate a group of nucleic acid fragments into a particular region of genome DNA. That is, a group of nucleic acid fragments comprises a nucleic acid fragment having either one of the pair of homologous recombination sequences corresponding to a particular region of genome DNA and a nucleic acid fragment having the other of the pair of homologous recombination sequences.

In the method of the present disclosure, in particular, a site-specific recombinase and a pair of recognition sequences recognized by such enzyme are used to cleave a target gene from the genome DNA. Thus, whether or not a group of nucleic acid fragments having target genes was accurately introduced into a particular region of the genome DNA can be determined. In the method of the present disclosure, specifically, a host cell in which the target gene flanked by the pair of recognition sequences recognized by the site-specific recombinase is cleaved from the genome DNA is selected from among the host cells into which the group of nucleic acid fragments had been introduced. According to the method of the present disclosure, at least one recognition sequence of a pair of recognition sequences is provided in a nucleic acid fragment other than the nucleic acid fragment comprising a target gene among the group of nucleic acid fragments. When the group of nucleic acid genes are inaccurately integrated into the genome DNA, accordingly, a target gene would not be flanked by a pair of recognition sequences, and a target gene would remain in the genome DNA. Therefore, whether or not the target gene has been cleaved from the genome DNA and whether or not a particular region has been accurately deleted from the genome DNA can be determined on the basis of the target gene expression.

In the method of the present disclosure, a site-specific recombinase is an enzyme that has activity of targeting a recognition sequence comprising a particular nucleotide sequence and causing recombination between a pair of recognition sequences. An example of a representative site-specific recombinase is a Cre recombinase, which is Type I topoisomerase derived from bacteriophage P1 (it may be simply referred to as "Cre"). Cre catalyzes site-specific recombination of DNA between a pair of loxP sites comprising particular sequences (i.e., Cre recognition sequences). A loxP recognition sequence is a 34-bp sequence comprising a 8-bp spacer sequence that determines the orientation and two 13-bp inverted repeat sequences that flank the spacer sequence. Cre is capable of recognizing the lox511 sequence comprising a nucleotide sequence different from the loxP recognition sequence and various variant lox sequences, such as lox2272 and loxFAS (Siegel, R. W. et al., 2001, FEBS letters, 499 (1-2), 147-53) and catalyzing site-specific recombination between such variant lox sequences.

In addition to Cre recombinase, examples of system of site-specific recombinases and recognition sequences include Flp recombinase and FRT sequence derived from the yeast 2μ plasmid (Broach, J. R. et al., 1982, Cell, 29 (1), 227-34), Dre recombinase and rox sequence derived from the Enterobacteria phage D6 (U.S. Pat. No. 7,422,889), R recombinase and RS sequence derived from a soy sauce yeast (*Zygosaccharomyces rouxii*) (Araki, H. et al., 1985, Journal of molecular biology, 182 (2), 191-203), and Gin recombinase and gix sequence derived from bacteriophage Mu (Maeser, S., et al., Molecular & general genetics: MGG, 230 (1-2), 170-6).

When two recognition sequences of a site-specific recombinase are present toward the same direction, a region between the recognition sequences would be circularly cleaved. When two enzyme recognition sequences are present toward opposite directions, the site-specific recombinase would invert a region between the recognition sequences.

A target gene refers to a nucleic acid to be introduced into the host genome. Accordingly, a target gene is not limited to a nucleotide sequence encoding a particular protein, and it encompasses nucleic acids comprising various nucleotide sequences, such as a nucleotide sequence encoding siRNA, a nucleotide sequence of a transcription regulatory region, such as a promoter or enhancer, that regulates the timing of transcription and the amount of production of transcription products, and a nucleotide sequence encoding transfer RNA (tRNA) or ribosome RNA (rRNA).

An example of a target gene is a so-called selection marker gene. Examples of selection marker genes include a drug-resistant gene that provides a host having susceptibility to a particular drug with resistance against such drug, a gene that encodes a fluorescent protein, a gene that encodes an enzyme catalyzing a coloring reaction, and an auxotrophic marker gene. Examples of drug-resistant genes include, but are not particularly limited to, antibiotic-resistant genes, such as a G418-resistant gene, a nourseothricin-resistant gene, a kanamycin-resistant gene, a hygromycin-resistant gene, a neomycin-resistant gene, an ampicillin-resistant gene, and an Aureobasidin A-resistant gene.

A target gene is not limited to the marker genes mentioned above, and it may be a site-specific recombinase gene. Specific examples include genes encoding the Cre recombinase, the Dre recombinase, and the Flp or Gin recombinase mentioned above. A site-specific recombinase gene is adequately selected in accordance with the recognition sequence used in the method of the present disclosure.

A target gene is integrated into genome DNA in an expressible state. A site-specific recombinase gene may be integrated into genome DNA together with a target gene in an expressible state, or a site-specific recombinase gene may be integrated into an expression vector and then introduced into the host in an expressible state. In an expressible state, a target gene or a site-specific recombinase gene is linked to a promoter, so that the gene is expressed under the control of a particular inducible promoter or a constitutive expression promoter in a host organism. In addition, cis elements, such as a promoter, a terminator, and, according to need, an enhancer, a splicing signal, a poly A addition signal, or a ribosome-binding (SD) sequence, can be ligated to the target gene.

A promoter for a target gene or a site-specific recombinase gene may be an inducible promoter or a constitutive expression promoter. An inducible promoter has functions of inducing expression under specific conditions. Examples of inducible promoters include, but are not particularly limited to, a promoter that induces expression in the presence of a particular substance, a promoter that induces expression under particular temperature conditions, and a promoter that induces expression in response to various types of stress. A promoter can be adequately selected in accordance with a host to be transformed.

Examples of inducible promoters include galactose-inducible GAL1 and GAL10 promoters, Tet-on/Tet-off system promoters that induce expression with the addition or removal of tetracycline or its derivative, and promoters of genes encoding heat shock proteins (HSP) such as HSP10, HSP60, and HSP90. As an inducible promoter, a CUP1 promoter that is activated with the addition of copper ions can be used. When a host is a prokaryotic cell such as *E. coli*, in addition, examples of inducible promoters include an IPTG-inducible lac promoter, a cold-shock-inducible cspA promoter, and an arabinose-inducible araBAD promoter.

A method for regulating target gene or site-specific recombinase gene expression is not limited to a method involving the use of a promoter, such as an inducible promoter or a constitutive expression promoter. For example, a method involving the use of a DNA recombinase may be employed. An example of a method that turns gene expression on or off with the use of a DNA recombinase is the FLEx switch method (A FLEX Switch Targets Channelrhodopsin-2 to Multiple Cell Types for Imaging and Long-Range Circuit Mapping, Atasoy et al., The Journal of Neuroscience, 28, 7025-7030, 2008). According to the FLEx switch method, a DNA recombinase is used to cause recombination that alters the promoter sequence orientation and turns the gene expression on or off.

FIG. 1 schematically shows an embodiment of the method of the present disclosure. In the method shown in FIG. 1, a first nucleic acid fragment 1 containing, as a target gene, a selection marker gene S, a second nucleic acid fragment 2 containing one recognition sequence M1 of a pair of recognition sequences recognized by a site-specific recombinase, and a third nucleic acid fragment 3 containing the other recognition sequence M2 are introduced into the host. As long as the nucleotide sequences of the first nucleic acid fragment 1 to the third nucleic acid fragment 3 are determined, each of such fragments can be prepared as a double-stranded DNA via chemical synthesis in accordance with a conventional technique. In the method of the present disclosure, a site-specific recombinase gene is introduced into the host in an expressible manner, although it is not shown in FIG. 1. A site-specific recombinase gene may be contained in the first nucleic acid fragment 1, or it may be contained in an expression vector separately prepared.

The second nucleic acid fragment 2 comprises a first homologous recombination sequence 4 that can undergo homologous recombination with the host genome DNA at one end and a second homologous recombination sequence 5 that can undergo homologous recombination with the first nucleic acid fragment 1 at the other end. The first nucleic acid fragment 1 comprises a third homologous recombination sequence 6 that can undergo homologous recombination with the second nucleic acid fragment 2 at one end and a fourth homologous recombination sequence 7 that can undergo homologous recombination with the third nucleic acid fragment 3 at the other end. The third nucleic acid fragment 3 comprises a fifth homologous recombination sequence 8 that can undergo homologous recombination with the first nucleic acid fragment 1 at one end and a sixth homologous recombination sequence 9 that can undergo homologous recombination with the host genome DNA at the other end.

The first homologous recombination sequence 4 of the second nucleic acid fragment 2 and the sixth homologous recombination sequence 9 of the third nucleic acid fragment 3 can be designed based on a region to be deleted from the genome DNA. When a region R is to be deleted from the genome DNA in FIG. 1, for example, the first homologous recombination sequence 4 is designed based on the sequence of a recombinant region 10 upstream of the region R, and the sixth homologous recombination sequence 9 is designed based on the sequence of a recombinant region 11 downstream of the region R.

The first homologous recombination sequence 4 of the second nucleic acid fragment 2 and the sixth homologous recombination sequence 9 of the third nucleic acid fragment 3 can be designed as an upstream region in a particular region of genome DNA and a downstream region continuous to the upstream region. Specifically, the recombinant region 10 and the recombinant region 11 can be designed as continuous regions (i.e., the region R is not present), and the first homologous recombination sequence 4 and the sixth homologous recombination sequence 9 can be designed to correspond to such regions. In such a case, the original genome DNA would not be deleted of any region, and a group of nucleic acid fragments comprising target genes would be inserted into the genome DNA.

The second homologous recombination sequence 5 of the second nucleic acid fragment 2 and the fifth homologous recombination sequence 8 of the third nucleic acid fragment 3 can be designed based on the nucleotide sequences at the both ends of the first nucleic acid fragment 1. The second homologous recombination sequence 5 of the second nucleic acid fragment 2 and the third homologous recombination sequence 6 of the first nucleic acid fragment 1 can be designed as any nucleotide sequences as long as such sequences can undergo homologous recombination. Also, the fifth homologous recombination sequence 8 of the third nucleic acid fragment 3 and the fourth homologous recombination sequence 7 of the first nucleic acid fragment 1 can be designed as any nucleotide sequences as long as such sequences can undergo homologous recombination. Specifically, the first nucleic acid fragment 1 can be designed to comprise sequences at the both ends other than the target gene (i.e., the third homologous recombination sequence 6 and the fourth homologous recombination sequence 7) as any common nucleotide sequences, regardless of the region R to be deleted and the selection marker gene S.

A region between the first homologous recombination sequence 4 of the second nucleic acid fragment 2 and the recombinant region 10 and a region between the sixth homologous recombination sequence 9 of the third nucleic acid fragment 3 and the recombinant region 11 have sequence identity that is high enough to undergo homologous recombination (crossing). Nucleotide sequence identity in each of the regions can be calculated using a conventional sequence comparison software, such as blastn. Nucleotide sequence identity in each of the regions may be 60% or higher. In some embodiments, sequence identity may be 80% or higher, 90% or higher, 95% or higher, and 99% or higher.

The length of the first homologous recombination sequence 4 of the second nucleic acid fragment 2 may be the same with or different from that of the sixth homologous recombination sequence 9 of the third nucleic acid fragment 3. The length of the first homologous recombination sequence 4 and that of the sixth homologous recombination sequence 9 need to be long enough to undergo homologous recombination (crossing) with the genome DNA. For example, such length may be 0.1 kb to 3 kb, 0.5 kb to 3 kb, and 0.5 kb to 2 kb.

The lengths of the second homologous recombination sequence 5 to the fifth homologous recombination sequence 8 of the first nucleic acid fragment 1 to the third nucleic acid fragment 3 may be the same with or different from one another, provided that these sequences can undergo homologous recombination. The lengths of the second homologous recombination sequence 5 to the fifth homologous recombination sequence 8 may be, for example, 30 b to 300 b. In some embodiments, the length may be 40 b to 200 b, or 50 b to 100 b.

Sequence identity between the third homologous recombination sequence 6 of the first nucleic acid fragment 1 and the second homologous recombination sequence 5 of the second nucleic acid fragment 2 and sequence identity between the fourth homologous recombination sequence 7 of the first nucleic acid fragment 1 and the fifth homologous recombination sequence 8 of the third nucleic acid fragment 3 need to be high enough to undergo homologous recombination (crossing). Nucleotide sequence identity in each of the regions can be calculated using a conventional sequence comparison software, such as blastn. Nucleotide sequence identity in each of the regions may be 60% or higher. In some embodiments, sequence identity may be 80% or higher, 90% or higher, 95% or higher, and 99% or higher.

The first nucleic acid fragment 1, the second nucleic acid fragment 2, and the third nucleic acid fragment 3 configured as described above are introduced into the host. As a result, homologous recombination takes place between the first nucleic acid fragment 1 and the genome DNA, between the first nucleic acid fragment 1 and the second nucleic acid fragment 2, between the first nucleic acid fragment 1 and the third nucleic acid fragment 3, and between the third nucleic acid fragment 3 and the genome DNA, as schematically shown in FIG. 1. Thus, the first nucleic acid fragment 1, the second nucleic acid fragment 2, and the third nucleic acid fragment 3 would be integrated into the genome DNA. This would result in deletion of the region R from the genome DNA.

Upon expression of the site-specific recombinase gene contained in the first nucleic acid fragment 1 or an expression vector, a region between the pair of recognition sequences M1 and M2 would be deleted. More specifically, the third homologous recombination sequence 6, the selection marker gene S, and the fourth homologous recombination sequence 7 between the pair of recognition sequences M1 and M2 would be deleted from the genome DNA, as shown in FIG. 2.

In the method of the present disclosure, the recognition sequence M1 is located on the second nucleic acid fragment 2, and the recognition sequence M2 is located on the third nucleic acid fragment 3. When the first nucleic acid fragment 1 to the third nucleic acid fragment 3 are not accurately integrated into the genome DNA, accordingly, the selection marker gene S would not be flanked by the pair of recognition sequences M1 and M2. Even if the site-specific recombinase gene is expressed, the selection marker gene S would remain in the genome DNA.

When the second nucleic acid fragment 2 is not integrated but the first nucleic acid fragment 1 and the third nucleic acid fragment 3 are integrated into a region other than the region R in the genome DNA as shown in FIG. 3, for example, the selection marker gene S would not be deleted and it would remain in the genome DNA even if the site-specific recombinase gene is expressed. With the use of a phenotype resulting from the selection marker gene S, such as drug resistance or fluorescence, as the indicator, whether or not the first nucleic acid fragment 1 to the third nucleic acid fragment 3 had been accurately integrated into the genome DNA, in other words, whether or not the region R had been accurately deleted, can be evaluated.

When the pair of recognition sequences M1 and M2 are present in the same nucleic acid fragment (the first nucleic acid fragment 1 in FIG. 1) to flank the selection marker gene as shown in FIG. 4, in contrast, the selection marker gene S flanked by the pair of recognition sequences M1 and M2 would be deleted from the genome DNA upon expression of the site-specific recombinase gene, regardless of whether a plurality of nucleic acid fragments had been integrated into the genome DNA accurately or inaccurately. In such a case, it is not possible to evaluate as to whether or not a plurality of nucleic acid fragments had been accurately integrated into the genome DNA using a phenotype resulting from the selection marker gene S, such as drug resistance or fluorescence, as the indicator. When the pair of recognition sequences M1 and M2 are present in the same nucleic acid fragment to flank the selection marker gene S as shown in FIG. 4, accordingly, it is necessary to subject the plurality of nucleic acid fragments to a nucleic acid amplification reaction, such as PCR, to verify that the target region had been deleted from the genome DNA.

As described above, the method of using the site-specific recombinase and its recognition sequence to remove the selection marker gene S from the genome DNA can be applied to the so-called marker recycle method. According to the marker recycle method, a plurality of genes are successively introduced or deleted, a selection marker gene used for a single instance of gene introduction or deletion is removed, and the same selection marker gene is used for the subsequent gene introduction or deletion.

The method of the present disclosure shown in FIGS. 1 to 3 can be applied to the marker recycle method. As shown in FIGS. 1 and 2, specifically, a transformant from which the particular region R had been removed is selected using the phenotype resulting from the expression of the selection marker gene S as an indicator, and the selection marker gene S is then removed using the site-specific recombinase and its recognition sequence. As described above, a transformant lacking a particular region R does not have the selection marker gene S. Thus, the first nucleic acid fragment 1 having the selection marker gene S may be used again to delete a region other than the region R. According to the marker recycle method, as shown in FIG. 3, it is possible to verify that the first nucleic acid fragment 1 to the third nucleic acid fragment 3 were not accurately integrated based on the expression of the selection marker gene S.

In the marker recycle method involving the use of the method of the present disclosure, in particular, the first nucleic acid fragment 1 having the selection marker gene S can be repeatedly used. According to the method of the present disclosure, as described above, the selection marker gene S is removed with the use of the site-specific recombinase and its recognition sequence, and the third homologous recombination sequence 6 and the fourth homologous recombination sequence 7 are removed at the same time. When the pair of recognition sequences M1 and M2 are present in the same nucleic acid fragment to flank the selection marker gene S as shown in FIG. 4, in contrast, the selection marker gene S may be deleted from a region between the pair of recognition sequences M1 and M2 with the aid of a site-specific recombinase. In such a case, the homologous recombination sequences 20 and 21 at the both ends of the nucleic acid fragment would remain in the genome DNA. When another region is to be deleted with the use of the nucleic acid fragment comprising the pair of recognition sequences M1 and M2 and the selection marker gene S again, as shown in FIG. 5, a newly introduced nucleic acid fragment may undergo homologous recombination with the homologous recombination sequences 20 and 21 remaining in the genome DNA.

According to the method of the present disclosure, in contrast, the third homologous recombination sequence 6 and the fourth homologous recombination sequence 7 in the first nucleic acid fragment 1 comprising the selection marker gene S would not remain in the genome DNA at the same time. Even if a region other than the region R is deleted with the use of the first nucleic acid fragment 1 comprising the selection marker gene S again, accordingly, it is possible to prevent a problem such that the first nucleic acid fragment 1 would be integrated into a site where the region R had existed. In the marker recycle method, accordingly, at least one recognition sequence of the pair of recognition sequences M1 and M2 may be provided in a nucleic acid fragment other than the first nucleic acid fragment 1 having the selection marker gene S. Thus, the first nucleic acid fragment 1 having the selection marker gene S can be repeatedly used.

The first nucleic acid fragment 1 can be repeatedly used. In other words, it is not necessary to prepare the first nucleic acid fragment 1 every time when the selection marker gene S is used a plurality of times in the marker recycle method. When the pair of recognition sequences M1 and M2 is present in the same nucleic acid fragment to flank the selection marker gene S as shown in FIG. 4, it is necessary to prepare nucleic acid fragments designed to constitute the homologous recombination sequences 20 and 21 comprising different nucleotide sequences in order to prevent the problem as shown in FIG. 5. Since the first nucleic acid fragment 1 can be repeatedly used in the method of the present disclosure, a procedure can be simplified when such method is applied to the marker recycle method.

According to the method shown in FIGS. 1 and 2, the second nucleic acid fragment 2 and the third nucleic acid fragment 3 were designed to comprise the recognition sequences M1 and M2, respectively. That is, both of the pair of recognition sequences M1 and M2 were designed to be located in nucleic acid fragments other than the first nucleic acid fragment 1 comprising the selection marker gene S. In the method of the present disclosure, in contrast, it is sufficient if the pair of recognition sequences M1 and M2 flanks the selection marker gene S, at least one of the pair of recognition sequences M1 and M2 is located on a nucleic acid fragment other than the first nucleic acid fragment 1 comprising the selection marker gene S, and the other thereof is located on the first nucleic acid fragment 1. For example, the recognition sequence M1 of the pair of recognition sequences M1 and M2 may be located on the first nucleic acid fragment 1 comprising the selection marker gene S, and the other recognition sequence M2 may be located on the third nucleic acid fragment 3, as shown in FIG. 6. In such a case, as shown in FIG. 7, the selection marker gene S and the fourth homologous recombination sequence 7 are deleted from a region between the pair of recognition sequences M1 and M2 by the action of the site-specific recombinase, but the third homologous recombination sequence 6 of the first nucleic acid fragment 1 would remain in the genome DNA.

Even if the third homologous recombination sequence 6 of the first nucleic acid fragment 1 remains in the genome DNA as shown in FIG. 7, as with the case shown in FIGS. 1 to 3, a phenotype resulting from the selection marker gene S, such as drug resistance or fluorescence, may be used as the indicator to evaluate as to whether or not the first nucleic acid fragment 1 to the third nucleic acid fragment 3 had been accurately integrated into the genome DNA, in other words, whether or not the region R had been accurately deleted. Even if the third homologous recombination sequence 6 of the first nucleic acid fragment 1 remains in the genome DNA as shown in FIG. 7, the first nucleic acid fragment 1 having the selection marker gene S would not be erroneously integrated into the same position. As described above, accordingly, it is possible to prevent erroneous integration of the first nucleic acid fragment 1 having the selection marker gene S in the marker recycle method.

In the method of the present disclosure, a plurality of nucleic acid fragments are not limited to the first nucleic acid fragment 1 to the third nucleic acid fragment 3, and 4 or more nucleic acid fragments may be used to introduce a target gene into a particular region of genome DNA. When the pair of recognition sequences M1 and M2 flanks the selection marker gene S and at least one of the pair of recognition sequences M1 and M2 is located on a nucleic acid fragment other than the first nucleic acid fragment 1 comprising the selection marker gene S, a phenotype resulting from the selection marker gene S, such as drug resistance or fluorescence, may be used as the indicator to evaluate as to whether or not a plurality of nucleic acid fragments had been accurately integrated into the genome DNA, in other words, whether or not the region R had been accurately deleted. As described above, accordingly, it is possible to prevent erroneous integration of the first nucleic acid fragment 1 having the selection marker gene S in the marker recycle method.

The method of the present disclosure can be applied to any host cell without particular limitation. Examples of host cells include fungi such as filamentous fungi and yeast, bacteria such as *E. coli* and *Bacillus subtilis*, plant cells, and animal cells including mammalian and insect cells. In particular, yeast host cells may be used. Examples of yeast include, but are not particularly limited to, yeast of *Saccharomyces*, yeast of *Kluyveromyces*, yeast of *Candida*, yeast of *Pichia*, yeast of *Schizosaccharomyces*, and yeast of *Hansenula*. More specifically, the method of the present disclosure can be applied to yeast species of *Saccharomyces*, such as *Saccharomyces cerevisiae, Saccharomyces bayanus*, and *Saccharomyces boulardii*.

Expression vectors comprising site-specific recombinase genes are not particularly limited. Examples of expression vectors that can be used include: YCp-type *E. coli*-yeast shuttle vectors such as pRS413, pRS414, pRS415, pRS416, YCp50, pAUR112, and pAUR123; Yep-type *E. coli*-yeast shuttle vectors such as YES2 and YEp13; YIp-type *E. coli*-yeast shuttle vectors such as pRS403, pRS404, pRS405, pRS406, pAUR101, and pAUR135; *E. coli*-derived plasmids, such as ColE-type plasmids such as pBR322, pBR325, pUC18, pUC19, pUC118, pUC119, pTV118N, pTV119N, pBluescript, pHSG298, pHSG396, and pTrc99A, p15A-type plasmids such as pACYC177 and pACYC184, and pSC101-type plasmids such as pMW118, pMW119, pMW218, and pMW219; *Agrobacterium*-derived plasmids such as pBI101; and *Bacillus subtilis*-derived plasmids such as pUB110 and pTP5.

In the method of the present disclosure, the first nucleic acid fragment 1 to the third nucleic acid fragment 3 or an expression vector can be introduced into a host cell by any method without particular limitation. An adequate method may be selected from among conventional techniques, such as the calcium chloride method, the competent cell method, the protoplast or spheroplast method, and the electropulse method.

In order to express a site-specific recombinase gene under the control of an inducible promoter, adequate conditions are determined in accordance with the inducible promoter. In the case that a galactose-inducible promoter, such as GAL1- or GAL10-inducible promoter, is used, for example, galactose is added to a medium used for culturing a host cell comprising the first nucleic acid fragment 1 to the third nucleic acid fragment 3 or the expression vector introduced therein, or the host cell is transferred to and cultured in a galactose-containing medium. Thus, a site-specific recombinase gene can be induced to express. In the case that a promoter of a gene encoding a heat shock protein (HSP) is used as an inducible promoter, heat shock is applied at a desired timing when culturing a host cell comprising the first nucleic acid fragment 1 to the third nucleic acid fragment 3 or the expression vector introduced therein. Thus, a site-specific recombinase gene can be induced to express at a desired timing.

Under the conditions in which an inducible promoter can induce gene expression, the first nucleic acid fragment 1 to the third nucleic acid fragment 3 or the expression vector may be introduced into a host cell, and a site-specific recombinase gene may be expressed under the control of the inducible promoter. In such a case, it is not necessary to transfer the host cell to an expression-inducible condition. Thus, a transformant can be obtained more easily.

In the method of the present disclosure, the first homologous recombination sequence 4 of the second nucleic acid fragment 2 and the sixth homologous recombination sequence 9 of the third nucleic acid fragment 3 are designed to comprise nucleotide sequences that are highly homologous to an upstream region and a downstream region of a particular gene. In such a case, a nucleic acid fragment comprising a target gene would be integrated into the genome via homologous recombination and the particular gene would be deleted from the genome. By observing a phenotype resulting from deletion of the particular gene, accordingly, whether or not a nucleic acid fragment comprising a target gene had been integrated into the genome can be determined. When the ADE1 gene is used as a particular gene, for example, the ADE1 gene would be deleted from the genome upon integration of a group of nucleic acid fragments comprising target genes into the genome. As a result, 5-aminoimidazole riboside is accumulated in the host, and a transformant is colored red by the polymerized polyribosyl aminoimidazole. By detecting a red color, accordingly, whether or not a group of nucleic acid fragments having target genes had been integrated into the host genome can be determined.

EXAMPLES

Hereafter, the present disclosure is described in greater detail with reference to the examples, although the technical scope of the present disclosure is not limited to the following examples.

Example 1

In this example, the haploid experimental yeast strain, *S. cerevisiae* BY4742, was used as a host.

Preparation of a GRE3-Destructive Linear Vector Set in which loxP and a Marker are Contained in the Same DNA Fragment In this example, as shown in FIG. 8, 3 types of plasmids each comprising a DNA fragment containing the 5'-homologous recombination region of the GRE3 gene (homologous sequence 1) and a DNA sequence to perform homologous recombination (homologous sequence 2); a DNA fragment containing a gene sequence having a G418-resistant gene (G418 marker) and a DNA recombinase Cre gene (not shown in FIG. 8) to perform loxP-sequence-site-specific recombination flanked by loxP sequences and, at both ends, DNA sequences to perform homologous recombination (homologous sequences 2 and 3); and a DNA fragment containing the DNA sequence to perform homologous recombination (homologous sequence 3) and a 3'-homologous recombination region of the GRE3 gene (homologous sequence 4) inserted therein were prepared. The homologous sequence 2 and the homologous sequence 3 were both of approximately 60 bp and designed on a primer sequence. Upon expression of the Cre gene, the G418 marker and the Cre gene flanked by two loxP sequences can be removed. DNA sequences can be amplified via PCR. In order to bind DNA fragments to each other, primers were artificially synthesized with the addition of a DNA sequence to overlap with an adjacent DNA sequence by approximately 15 bp (Table 1).

With the use of the primers described above and the genome or synthetic DNA of the *S. cerevisiae* BY4742 strain as a template, the target DNA fragments were amplified, the DNA fragments were successively bound to each other using the In-Fusion HD Cloning Kit or the like, and the resultant was cloned into the pUC19 vector to prepare the 3 types of target plasmids. The resulting plasmids were designated as pUC-5U_GRE3-homologous sequence 2, pUC-homologous sequence 2-loxP-P_ERG1-G418-T_URA3-T_CYC1-Cre-P_GAL1-loxP-homologous sequence 3, and pUC-homologous sequence 3-3U_GRE3. A set of the 3 types of plasmids was designated as the pUC-gre3::loxPin-G418-Cre vector set.

TABLE 1

| Amplified DNA fragment | Primer sequence (5'-3') | SEQ ID NO: |
|---|---|---|
| | pUC-5U_GRE3-homologous sequence 2 | |
| Fragment containing GRE3 5'-homologous recombination sequence and homologous sequence 2 | GTGGCCCGGGAGAGACAGTTTAGTAGTGACTCGCGGCCAGTTGGGG CTAAACGAGATTTGGAATATTG | 1 |
| | CAATCACAGGGCGGGAAATAAGCTACAATTAACGCCAAAAAATCTT TAAAAAATTTCCAATTTTCCTTTACGATTTATATTACAG | 2 |
| Fragment containing pUC19 and homologous sequence 2 | CCCGCCCTGTGATTGAGGCGGGATGGTGTCCCCACAGTCACGACGT TGTAAAACG | 3 |
| | TCTCTCCCGGGCCACGACGCTAGGCCAGTACCTCCACTCTCAGTAC AATCTGCTCTGATG | 4 |
| | pUC-homologous sequence 2-loxP-P_REG1-G418-T_URA3-T_CY1-Cre-P_GAL1-loxP-homologous sequence 3 | |
| Fragment containing homologous sequence 2, loxP sequence, and ERG1 promoter | GGGATGGTGTCCCCACAGTTACCGTTCGTATAGCATACATTATACG AAGTTATGTCTCTTGCAGAACACAATAAGTG | 5 |
| | GTTGAATATGGCTCATCCTTGTATTACTCGTTTGTTCTGTTTCTAT | 6 |
| Fragemnt containing G418 | ATGAGCCATATTCAACGGGAAAC | 7 |
| | TTTAGTAGACATGCATTACAACCAATTAACCAATTCTG | 8 |
| Fragment containing URA3 terminator | TGCATGTCTACTAAACTCACAAATTAGAGCTTCAATT | 9 |
| | GGGTAATAACTGATATAATTAAATTGAAGCTC | 10 |
| Fragment containing CYC1 terminator | TATCAGTTATTACCCAGCTTGCAAATTAAAGCCTTCG | 11 |
| | TTAGTTATGTCACGCTTACATTCACG | 12 |
| Fragment containing Cre gene (posterior region) and COX5B intron | GCGTGACATAACTAATCAATCACCATCTTCCAACAATC | 13 |
| | CCATTTACTAACATTCGAGGTGTACAAGCACAAGTTTTGCAGGCTT TCGAAAGAACTGATTTCGATC | 14 |
| Fragment containing COX5B intron and Cre gene (anterior region) | GAATGTTAGTAAATGGATATCTTTTAAAACTCAAAACAAAAATCAG TGTTTGTTATACATGCCAAAGCCTGCTTAGCTCTTTCAC | 15 |
| | CAAGGAGAAAAAACCATGTCTAACTTGTTGACTGTTC | 16 |
| Fragment containing GAL1 promoter, loxP sequence, and homologous sequence 3 | TGGTTTTTTCTCCTTGACGTTAAAGTATAG | 17 |
| | CAGTCGTAGATGCGTAAAATACCGTTCGTATAATGTATGCTATACG AAGTTATACGGATTAGAAGCCGCCG | 18 |
| Fragment containing pUC19 and homologous sequences 2 and 3 | ACGCATCTACGACTGTGGGTCCCGTGGAGAAATGTATGAAACCCTG TATGGAGAGTGATTCAGTCACGACGTTGTAAAACGAC | 19 |
| | TGGGGACACCATCCCGCCTCAATCACAGGGCGGGAAATAAGCTACA ATTAACGCCAAACTCTCAGTACAATCTGCTCTG | 20 |
| | pUC-homologous sequence 3-3U_GRE3 | |
| Fragment containing GRE3 3'-homologous recombination sequence and homologous sequence 3 | CGTGGAGAAATGTATGAAACCCTGTATGGAGAGTGATTCAGTTCCA GCCAGTAAAATCCATACTC | 21 |
| | AGTGCGTCGGCAGTACCGGATCCTAAAGCCGATTCAAGAAAGTCT TTTTGCCAGCCAGTCC | 22 |
| Fragment containing pUC19 and homologous sequenc 3 | TACTGCCGACGCACTTTAGAACGGCCACCGTCCTCAGTCACGACGT TGTAAAACG | 23 |
| | ATACATTTCTCCACGGGACCCACAGTCGTAGATGCGTACTCTCAGT ACAATCTGCTCTG | 24 |

Preparation of a GRE3-Destructive Linear Vector Set (3 Fragments) in which loxP and a Marker are Contained in Different DNA Fragments In this example, as shown in FIG. 9, 3 types of plasmids each comprising a DNA fragment containing the 5'-homologous recombination region of the GRE3 gene (homologous sequence 1), one loxP sequence and a DNA sequence to perform homologous recombination (homologous sequence 5); a DNA fragment containing a gene sequence having a G418-resistant gene (G418 marker), the DNA recombinase Cre gene, and, at both ends, DNA sequences to perform homologous recombination (homologous sequences 5 and 6); and a DNA fragment containing the DNA sequence to perform homologous recombination (homologous sequence 6), the other loxP sequence, and a 3'-homologous recombination region of the GRE3 gene (homologous sequence 4) inserted therein were prepared. The homologous sequence 2 and the homologous sequence 3 were both of approximately 60 bp and designed on a primer sequence. The G418 marker and the Cre gene are flanked by two loxP sequences located on adjacent fragments. Upon expression of the Cre gene, the G418 marker, the Cre gene, and the homologous sequences 2 and 3 can be removed. DNA sequences can be amplified via PCR. In order to bind DNA fragments to each other, primers were synthesized with the addition of a DNA sequence so as to overlap with the adjacent DNA sequence by approximately 15 bp (Table 2).

With the use of the primers described above and the genome or synthetic DNA of the *S. cerevisiae* BY4742 strain as a template, the target DNA fragments were amplified, the DNA fragments were successively bound to each other using the In-Fusion HD Cloning Kit or the like, and the resultant was cloned into the pUC19 vector to prepare the 3 types of target plasmids. The resulting plasmids were designated as pUC-5U_GRE3-loxP-homologous sequence 5, pUC-homologous sequence 5-P_REG1-G418-T_URA3-T_CYC1-Cre-P_GAL1-homologous sequence 6, and pUC-homologous sequence 6-loxP-3U_GRE3. A set of the 3 types of plasmids was designated as the pUC-gre3::loxPout-G418-Cre vector set.

TABLE 2

| Amplified DNA fragment | Primer sequence (5'-3') | SEQ ID NO: |
|---|---|---|
| | pUC-5U_GRE3-loxP-homologous sequence 5 | |
| Fragment containing GRE3 5'-homologous recombination sequence, loxP, and homologous sequence 5 | GTGGCCCGGGAGAGACAGTTTAGTAGTGACTCGCGGCCAGTTGGGGC TAAACGAGATTTGGAATATTGGGGCTAAACGAGATTTGGAATATTG | 25 |
| | GCCTTCACATATAGTATAACTTCGTATAATGTATGCTATACGAACGG TAAAAATCTTTAAAAAATTTCCAATTTTCCTTTACGATTTATATTAC AGTATTTTCC | 26 |
| Fragment containing pUC19 and homologous sequence 5 | ACTATATGTGAAGGCATGGCTATGGCACGGCAGACATTCCGCCAGAT CATCAATAGGCACCAGTCACGACGTTGTAAAACG | 27 |
| | TCTCTCCCGGGCCACGACGCTAGGCCAGTACCTCCACTCTCAGTACA ATCTGCTCTGATG | 28 |
| | pUC-homologous sequence 5-P_REG1-G418-T_URA3-T_CYC1-Cre-P_GAL1-homologous sequence 6 | |
| Fragment containing homologous sequence 5 and ERG1 promoter | TGGCACGGCAGACATTCCGCCAGATCATCAATAGGCACCAGTGTCTC TTGCAGAACACAATAAG | 29 |
| | GTTGAATATGGCTCATCCTTGTATTACTCGTTTGTTCTGTTTCTATT C | 30 |
| Fragment containing G418 | ATGAGCCATATTCAACGGGAAAC | 31 |
| | TTTAGTAGACATGCATTACAACCAATTAACCAATTCTG | 32 |
| Fragment containing URA3 terminator | TGCATGTCTACTAAACTCACAAATTAGAGCTTCAATT | 33 |
| | GGGTAATAACTGATATAATTAAATTGAAGCTC | 34 |
| Fragment containing CYC1 terminator | TATCAGTTATTACCCAGCTTGCAAATTAAAGCCTTCG | 35 |
| | TTAGTTATGTCACGCTTACATTCACG | 36 |
| Fragment containing Cre gene (posterior region) and COX5B intron | GCGTGACATAACTAATCAATCACCATCTTCCAACAATC | 37 |
| | CCATTTACTAACATTCGAGGTGTACAAGCACAAGTTTTGCAGGCTTT CGAAAGAACTGATTTCGATC | 38 |
| Fragment containing COX5B intron and Cre gene (anterior region) | GAATGTTAGTAAATGGATATCTTTTAAAACTCAAAACAAAAATCAGT GTTTGTTATACATGCCAAAGCCTGCTTAGCTCTTTCAC | 39 |
| | CAAGGAGAAAAAACCATGTCTAACTTGTTGACTGTTC | 40 |
| Fragment containing GAL1 promoter and homologous sequence 6 | TGGTTTTTTCTCCTTGACGTTAAAGTATAG | 41 |
| | GAATCATTTAGACACGGGCATCGTCCTCTCGAAAGGTGAAAAACGGA TTAGAAGCCGC | 42 |
| Fragment containing pUC19 and homologous sequences 5 and 6 | GTGTCTAAATGATTCGACCAGCCTAAGAATGTTCAACCAGTCACGAC GTTGTAAAACG | 43 |
| | ATGTCTGCCGTGCCATAGCCATGCCTTCACATATAGTACTCTCAGTA CAATCTGCTCTG | 44 |
| | pUC-homologous sequence 6-loxP-3U_GRE3 | |
| Fragment containing GRE3 3'-homologous recombination sequence, loxP, and homologous sequence 6 | CTAAGAATGTTCAACATAACTTCGTATACGCATACATTATACGAACG GTACAGTTCCAGCCAGTAAAATCC | 45 |
| | AGTGCGTCGGCAGTACCGGATCCTAAAGCCGATTCAAGAAAAGTCTT TTTGCCAGCCAGTCC | 46 |
| Fragment containing pUC19 and homologous sequence 3 | TACTGCCGACGCACTTTAGAACGGCCACCGTCCTCAGTCACGACGTT GTAAAACG | 47 |
| | GTTGAACATTCTTAGGCTGGTCGAATCATTTAGACACGGGCATCGTC CTCTCGAAAGGTGACTCTCAGTACAATCTGCTC | 48 |

Figure 10:
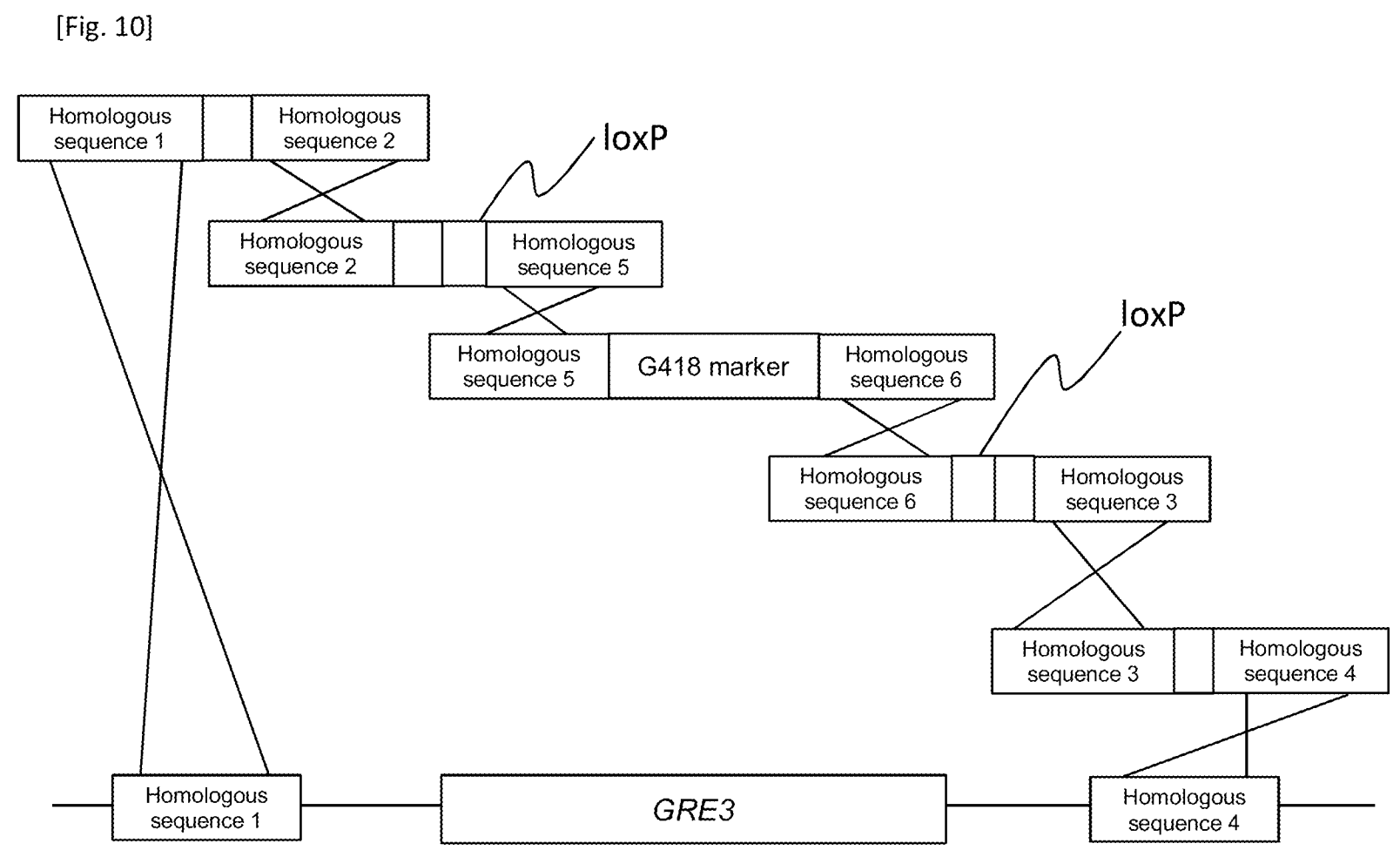

Preparation of a GRE3-Destructive Linear Vector Set (5 Fragments) in which loxP and a Marker are Contained in Different DNA Fragments In this example, as shown in FIG. 10, a GRE3-destructive linear vector set comprising 5 fragments was prepared. In this example, 2 types of plasmids each comprising a DNA fragment containing the loxP sequence and, at both ends, the homologous sequence 2 and the homologous sequence 5 and a DNA fragment containing the loxP sequence and, at both ends, the homologous sequence 6 and the homologous sequence 3 inserted therein were prepared. A 3'-downstream region of the ALD4 gene is inserted in a region between the homologous sequence 2 and the loxP sequence, and a 3'-downstream region of the ALD6 gene is inserted in a region between the loxP sequence and the homologous sequence 3 as dummy sequences so as to extend the length of the DNA fragment. DNA sequences can be amplified via PCR. In order to bind DNA fragments to each other, primers were synthesized with the addition of a DNA sequence so as to overlap with the adjacent DNA sequence by approximately 15 bp (Table 3).

With the use of the primers described above and the genome or synthetic DNA of the *S. cerevisiae* BY4742 strain as a template, the target DNA fragments were amplified, the DNA fragments were successively bound to each other using the In-Fusion HD Cloning Kit or the like, and the resultant was cloned into the pUC19 vector to prepare the 2 types of target plasmids. The resulting plasmids were designated as pUC-homologous sequence 2-loxP-dummy 1-homologous sequence 5 and pUC-homologous sequence 6-loxP-dummy 2-homologous sequence 3. A set of the 5 plasmids comprising pUC-homologous sequence 2-dummy 1-loxP-homologous sequence 5, pUC-homologous sequence 6-loxP-dummy 2-homologous sequence 3, pUC-5U_GRE3-homologous sequence 2 designed in advance (FIG. 8), pUC-homologous sequence 5-P_REG1-G418-T_URA3-T_CYC1-Cre-P_GAL1-homologous sequence 6 (FIG. 9), and pUC-homologous sequence 3-3U_GRE3 (FIG. 8) was designated as the pUC-gre3::loxPout-G418-Cre (5 fragments) vector set.

TABLE 3

| Amplified DNA fragment | Primer sequence (5'-3') | SEQ ID NO: |
|---|---|---|
| pUC-homologous sequence 2-dummy 1-loxP-homologous sequence 5 | | |
| Fragment containing homologous sequence 2, loxP, 3'-downstream region of ALD4 gene, and homologous sequence 5 | ATTTCCCGCCCTGTGATTGAGGCGGGATGGTGTCCCCACAGTGG TCATCAATAAGCCTGG | 49 |
| | GCCTTCACATATAGTATAACTTCGTATAATGTATGCTATACGAA CGGTAAAAAGATATTTCCAGTGCTAAGGTCAAC | 50 |
| Fragment containing pUC19, homologous sequence 2, and homologous sequence 5 | ACTATATGTGAAGGCATGGCTATGGCACGGCAGACATTCCGCCA GATCATCAATAGGCACCAGTCACGACGTTGTAAAAC | 51 |
| | CACAGGGCGGGAAATAAGCTACAATTAACGCCAAACTCTCAGTA CAATCTGCTC | 52 |
| pUC-homologous sequence 6-loxP-dummy 2-homologous sequenc 3 | | |
| Fragment containing homologous sequence 6, loxP, 3'-downstream region of ALD6 gene, and homologous sequence 3 | CTAAGAATGTTCAACATAACTTCGTATAGCATACATTATACGAA CGGTACAGTTGTACCAACCTGCATTTC | 53 |
| | ATACATTTCTCCACGGGACCCACAGTCGTAGATGCGTAAAAGCT CACTTGTTTCTTGATTTTTTAG | 54 |
| Fragment containing pUC19, homologous sequence 6, and homologous sequence 3 | CGTGGAGAAATGTATGAAACCCTGTATGGAGAGTGATTCAGTCA CGACGTTGTAAAACG | 55 |
| | GTTGAACATTCTTAGGCTGGTCGAATCATTTAGACACGGGCATC GTCCTCTCGAAAGGTGACTCTCAGTACAATCTGCTCTG | 56 |

Figure 11:
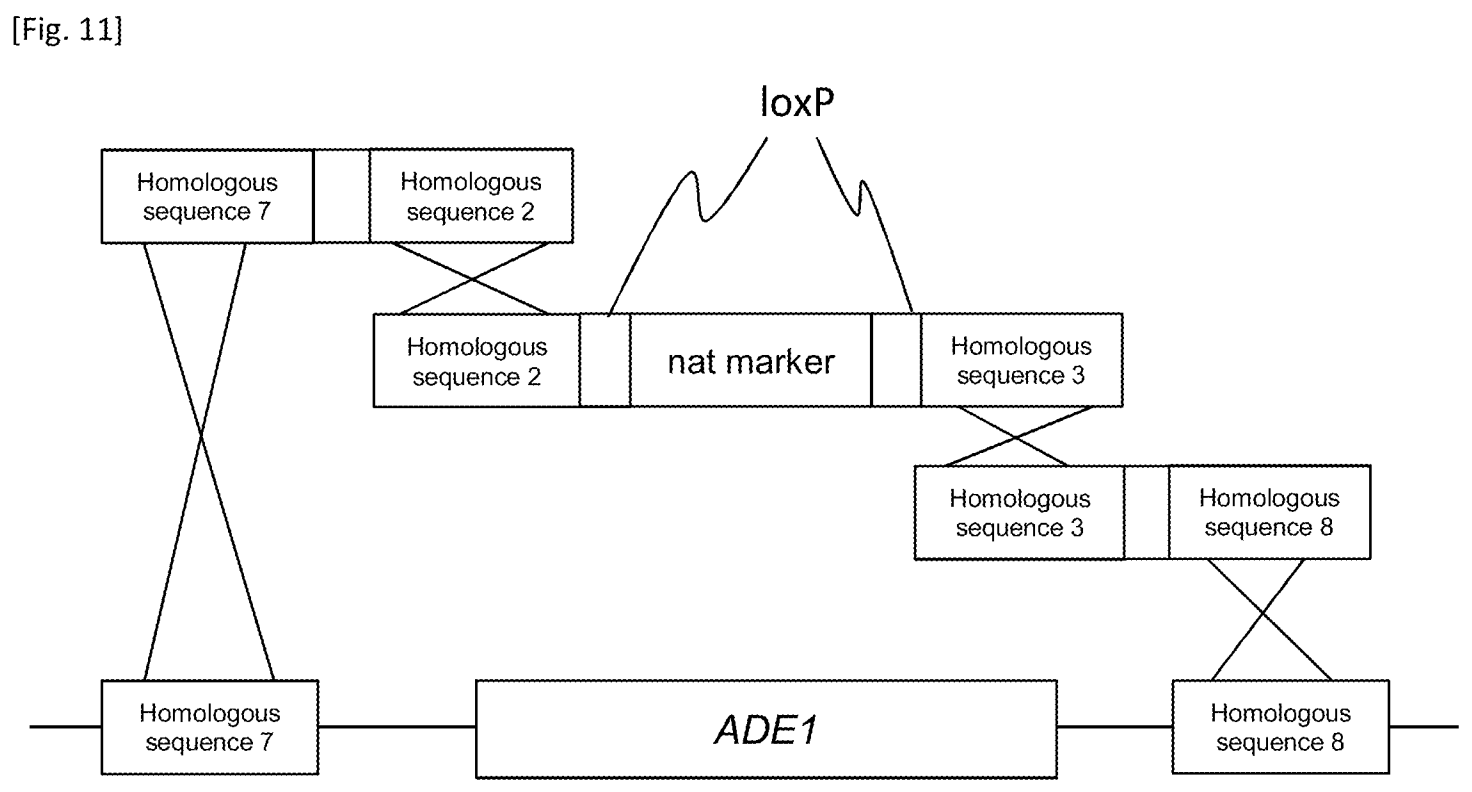

Preparation of an ADE1-Destructive Linear Vector Set in which loxP and a Marker are Contained in the Same DNA Fragment In this example, as shown in FIG. 11, 3 types of plasmids each comprising a DNA fragment containing a 5'-homologous recombination region of the ADE1 gene (homologous sequence 7) and a DNA sequence to perform homologous recombination (homologous sequence 2); a DNA fragment containing the nourseothricin-resistant gene (nat1: nat marker) and the DNA recombinase Cre gene (not shown) flanked by the loxP sequences and, at both ends, DNA sequences to perform homologous recombination (homologous sequences 2 and 3); and a DNA fragment containing a 3'-homologous recombination region of the ADE1 gene (homologous sequence 8) and a DNA sequence to perform homologous recombination (homologous sequence 3) inserted therein were prepared. Upon expression of the Cre gene, the nat marker and the Cre gene flanked by a pair of loxP sequences can be removed. DNA sequences can be amplified via PCR. In order to bind DNA fragments to each other, primers were synthesized with the addition of a DNA sequence so as to overlap with the adjacent DNA sequence by approximately 15 bp (Table 4).

With the use of the primers described above and the genome or synthetic DNA of the S. cerevisiae BY4742 strain as a template, the target DNA fragments were amplified, the DNA fragments were successively bound to each other using the In-Fusion HD Cloning Kit or the like, and the resultant was cloned into the pUC19 vector to prepare the 3 types of target plasmids. The resulting plasmids were designated as pUC-5U_ADE1-homologous sequence 2, pUC-homologous sequence 2-loxP-P_PMA1-nat1-T_LEU2-P_GAL1-Cre-T_CYC1-loxP-homologous sequence 3, and pUC-homologous sequence 3-3U_ADE1. A set of the 3 types of plasmids was designated as the pUC-ade1::loxPin-nat1-Cre vector set.

TABLE 4

| Amplified DNA fragment | Primer sequence (5'-3') | SEQ ID NO: |
|---|---|---|
| pUC-5U_ADE1-homologous sequence 2 | | |
| Fragment containing ADE1 5'-homologous recombination sequence and homologous sequence 2 | CGTGGCCCGGGAGAGACAGTTTAGTAGTGACTCGCGGCCAGTA TGAGTCGGGCAATTCCG | 57 |
| | CAATCACAGGGCGGGAAATAAGCTACAATTAACGCCAAAAAAT ATCGTTAATATTTCGTATGTGTATTCTTTGTAAG | 58 |
| Fragment containing pUC19 and homologous sequence 2 | CCCGCCCTGTGATTGAGGCGGGATGGTGTCCCCACAGTCACGA CGTTGTAAAACG | 59 |
| | CTCTCCCGGGCCACGACGCTAGGCCAGTACACTCTCAGTACAA TCTGCTC | 60 |
| Fragment containing pUC19 and homologous sequence 2 | | |
| Fragment containing homologous sequence 2, loxP sequence, and PMA1 promoter | GGGATGGTGTCCCCACAGTTACCGTTCGTATAGCATACATTAT ACGAAGTTATGTTACTCTCACACTCTTTAGTTC | 61 |
| | TCACCGAAATCTTCATATTGATATTGTTCGATAATTAAATCTT TCTTATC | 62 |
| Fragment containing nat1 | ATGAAGATTTCGGTGATCCCTG | 63 |
| | TTAGGCGTCATCCTGTGCTC | 64 |
| Fragment containing LEU2 terminator | CAGGATGACGCCTAAAAAGATTCTCTTTTTTTATGATATTTGT AC | 65 |
| | AGGAATCATAGTTTCATGATTTTCTGTTAC | 66 |

TABLE 4-continued

| Amplified DNA fragment | Primer sequence (5'-3') | SEQ ID NO: |
|---|---|---|
| Fragment containing GAL1 promoter | GAAACTATGATTCCTACGGATTAGAAGCCGCCG | 67 |
| | TGGTTTTTTCTCCTTGACGTTAAAGTATAG | 68 |
| Fragment containing Cre gene (anterior region) and COX5B intron | CAAGGAGAAAAAACCATGTCTAACTTGTTGACTGTTC | 69 |
| | CCATTTACTAACATTCGAGGTGTACAAGCACAAGTTTTGCAGG CTTTCGAAAGAACTGATTTCGATC | 70 |
| Fragment containing Cre gene (posterior region) | GTTTGTTATACATGCCAAAGCCTGCTTAGCTCTTTC | 71 |
| | CAAGGAGAAAAAACCATGTCTAACTTGTTGACTGTTC | 72 |
| Fragment containing CYC1 terminator, loxP sequence, and homologous sequence 3 | TGGTTTTTTCTCCTTGACGTTAAAGTATAG | 73 |
| | CAGTCGTAGATGCGTAAAATACCGTTCGTATAATGTATGCTAT AC | 74 |
| Fragment containing pUC19 and homologous sequences 2 and 3 | ACGCATCTACGACTGTGGGTCCCGTGGAGAAATGTATGAAACC CTGTATGGAGAGTGATTCAGTCACGACGTTGTAAAACGAC | 75 |
| | TGGGGACACCATCCCGCCTCAATCACAGGGCGGGAAATAAGCT ACAATTAACGCCAAACTCTCAGTACAATCTGCTCTG | 76 | pUC-homologous sequence 3-3U_ADE1

| Amplified DNA fragment | Primer sequence (5'-3') | SEQ ID NO: |
|---|---|---|
| Fragment containing ADE1 3'-homologous recombination sequence and homologous sequence 3 | CGTGGAGAAATGTATGAAACCCTGTATGGAGAGTGATTCAGTA TTCATACATACCCGTATG | 77 |
| | AGTGCGTCGGCAGTACCGGATCCTAAAGCCGATTCAAGAAAAT GACCGGATGAAACCACCG | 78 |
| Fragment containing pUC19 and homologous sequence 3 | TACTGCCGACGCACTTTAGAACGGCCACCGTCCTCAGTCACGA CGTTGTAAAACG | 79 |
| | ATACATTTCTCCACGGGACCCACAGTCGTAGATGCGTACTCTC AGTACAATCTGCTCTG | 80 |

Preparation of an ADE1-Destructive Linear Vector Set in which loxP and a Marker are Contained in Different DNA Fragments In this example, as shown in FIG. 12, 3 types of plasmids each comprising a DNA fragment containing a 5'-homologous recombination region of the ADE1 gene (homologous sequence 7), the loxP sequence, and a homologous sequence to perform homologous recombination (homologous sequence 2); a DNA fragment containing a gene sequence having the nourseothricin-resistant gene (nat1) (nat marker), the DNA recombinase Cre gene, and, at both ends, DNA sequences to perform homologous recombination (homologous sequences 2 and 3); and a DNA fragment containing a 3'-homologous recombination region of the ADE1 gene (homologous sequence 8), the loxP sequence, and a homologous sequence to perform homologous recombination (homologous sequence 3) inserted therein were prepared. The nat marker and the Cre gene are flanked by the loxP sequences contained in the adjacent fragments. Upon expression of the Cre gene, the nat marker and the Cre gene can be removed. DNA sequences can be amplified via PCR. In order to bind DNA fragments to each other, primers were synthesized with the addition of a DNA sequence so as to overlap with the adjacent DNA sequence by approximately 15 bp (Table 5).

With the use of the primers described above and the genome or synthetic DNA of the S. cerevisiae BY4742 strain as a template, the target DNA fragments were amplified, the DNA fragments were successively bound to each other using the In-Fusion HD Cloning Kit or the like, and the resultant was cloned into the pUC19 vector to prepare the 3 types of target plasmids. The resulting plasmids were designated as pUC-5U_ADE1-loxP-homologous sequence 2, pUC-homologous sequence 2-P_PMA1-nat1-T_LEU2-P_GAL1-Cre-T_CYC1-homologous sequence 3, and pUC-homologous sequence 3-loxP-3U_ADE1. A set of the 3 types of plasmids was designated as the pUC-ade1::loxPout-nat1-Cre vector set.

TABLE 5

| Amplified DNA fragment | Primer sequence (5'-3') | SEQ ID NO: |
|---|---|---|
| pUC-5U_ADE1-loxP-homologous sequence 5 | | |
| Fragment containing ADE1 5'-homologous recombination sequence, loxP, and homologous sequence 5 | CGTGGCCCGGGAGAGACAGTTTAGTAGTGACTCGCGGCCAG TATGAGTCGGGCAATTCCG | 81 |
| | GCCTTCACATATAGTATAACTTCGTATAATGTATGCTATAC GAACGGTAAAATATCGTTAATATTTCGTATGTGTATTCTTT GTAAGCAATG | 82 |
| Fragment containing pUC19 and homologous sequence 5 | ACTATATGTGAAGGCATGGCTATGGCACGGCAGACATTCCG CCAGATCATCAATAGGCACCAGTCACGACGTTGTAAAAC | 83 |
| | TCTCTCCCGGGCCACGACGCTAGGCCAGTACCTCCACTCTC AGTACAATCTGCTCTGATG | 84 |
| pUC-homologous sequence 5-P_PMA1-nat1-T_LEU2-P_GAL1-Cre-T_CYC1-homologus sequence 6 | | |
| Fragment containing homologous sequence 5 and PMA1 promoter | TGGCACGGCAGACATTCCGCCAGATCATCAATAGG | 85 |
| | TCACCGAAATCTTCATATTGATATTGTTCGATAATTAAATC TTTCTTATC | 86 |
| Fragment containing nat1 | ATGAAGATTTCGGTGATCCCTG | 87 |
| | TTAGGCGTCATCCTGTGCTC | 88 |

TABLE 5-continued

| Amplified DNA fragment | Primer sequence (5'-3') | SEQ ID NO: |
|---|---|---|
| Fragment containing LEU2-terminator | CAGGATGACGCCTAAAAAGATTCTCTTTTTTTATGATATTTGTAC | 89 |
| | AGGAATCATAGTTTCATGATTTTCTGTTAC | 90 |
| Fragment containing GAL1 promoter | GAAACTATGATTCCTACGGATTAGAAGCCGCCG | 91 |
| | TGGTTTTTTCTCCTTGACGTTAAAGTATAG | 92 |
| Fragment containing Cre gene (anterior region) and COX5B intron | CAAGGAGAAAAAACCATGTCTAACTTGTTGACTGTTC | 93 |
| | GAATGTTAGTAAATGGATATCTTTTAAAACTCAAAACAAAAATCAGTGTTTGTTATACATGCCAAAGCCTGCTTAGCTCTTTCAC | 94 |
| Fragment containing COX5B intron and Cre gene (posterior region) | CCATTTACTAACATTCGAGGTGTACAAGCACAAGTTTTGCAGGCTTTCGAAAGAACTGATTTCGATC | 95 |
| | GCGTGACATAACTAATCAATCACCATCTTCCAACAATC | 96 |
| Fragment containing CYC1 terminator and homologous sequence 6 | TTAGTTATGTCACGCTTACATTCACG | 97 |
| | GAATCATTTAGACACGGGCATCGTCCTCTCGAAAGGTGAAAAAGCTTGCAAATTAAAGCCTTCG | 98 |
| Fragment containing pUC19 and homologous sequences 5 and 6 | GTGTCTAAATGATTCGACCAGCCTAAGAATGTTCAACCAGTCACGACGTTGTAAAACG | 99 |
| | ATGTCTGCCGTGCCATAGCCATGCCTTCACATATAGTACTCTCAGTACAATCTGCTCTG | 100 | pUC-homologous sequence 6-loxP-3U_ADE1

| Amplified DNA fragment | Primer sequence (5'-3') | SEQ ID NO: |
|---|---|---|
| Fragment containing ADE1 3'-homologous recombinant sequence, loxP, and homologous sequence 6 | CTAAGAATGTTCAACATAACTTCGTATAGCATACATTATACG | 101 |
| | AGTGCGTCGGCAGTACCGGATCCTAAAGCCGATTCAAGAAAATGACCGGATGAAACCACCG | 102 |
| Fragment containing pUC19 and homologous sequence 6 | TACTGCCGACGCACTTTAGAACGGCCACCGTCCTCAGTCACGACGTTGTAAAACG | 103 |
| | GTTGAACATTCTTAGGCTGGTCGAATCATTTAGACACGGGCATCGTCCTCTCGAAAGGTGACTCTCAGTACAATCTGCTC | 104 |

Figure 13:
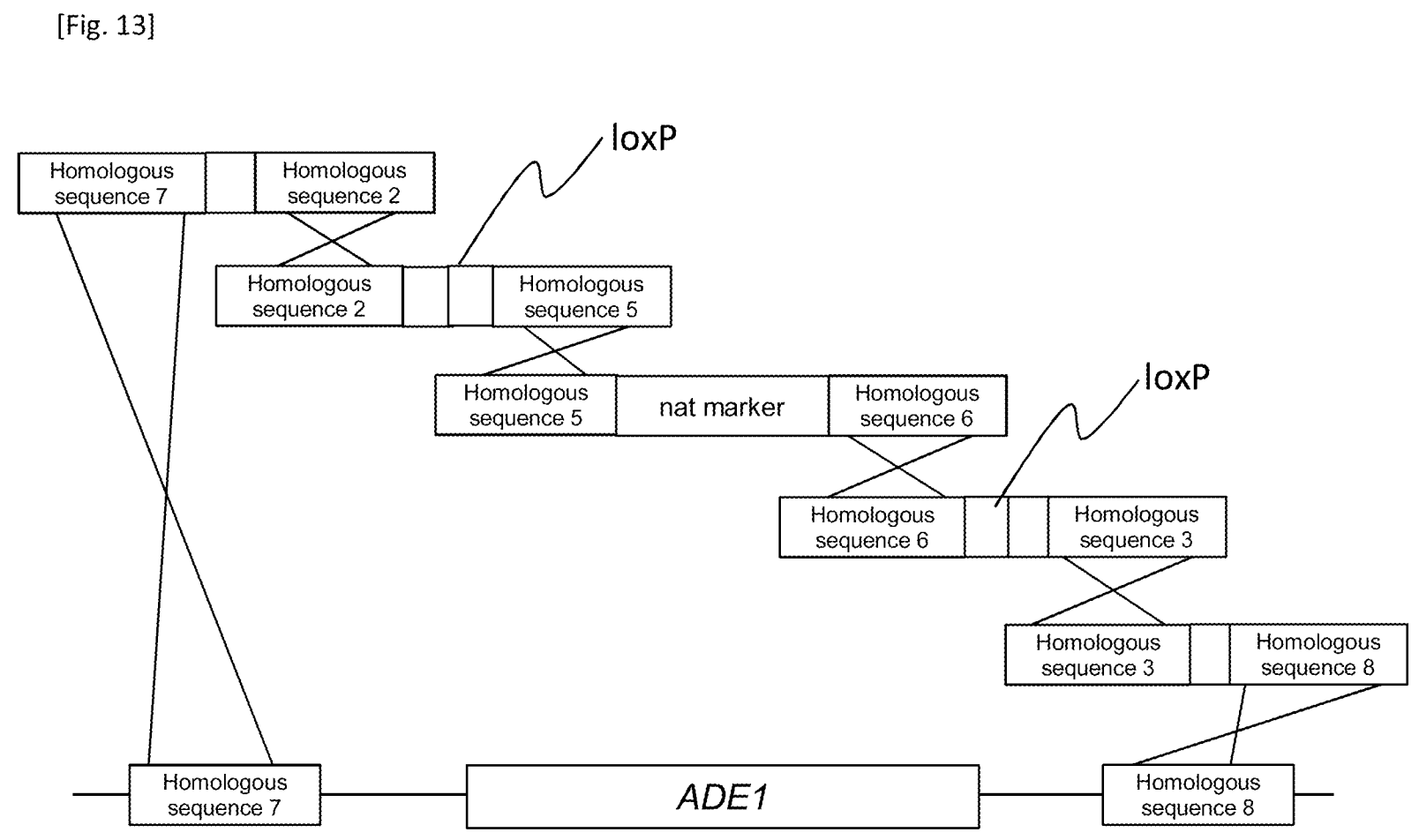

Preparation of an ADE1-Destructive Linear DNA Fragment Set (5 Fragments) in which loxP and a Marker are Contained in Different DNA Fragments In this example, as shown in FIG. 13, 2 types of plasmids each comprising a DNA fragment containing the loxP sequence and, at both ends, the homologous sequence 2 and the homologous sequence 5; and a DNA fragment containing the loxP sequence and, at both ends, the homologous sequence 6 and the homologous sequence 3 inserted therein were prepared. In these DNA fragments, a 5'-upstream region of the PDC6 gene is inserted in a region between the homologous sequence 2 and the loxP sequence, and a 5'-upstream region of the SED1 gene is inserted in a region between the loxP sequence and the homologous sequence 3 as dummy sequences so as to merely extend the length. DNA sequences can be amplified via PCR. In order to bind DNA fragments to each other, primers were synthesized with the addition of a DNA sequence so as to overlap with the adjacent DNA sequence by approximately 15 bp (Table 6).

With the use of the primers described above and the genome or synthetic DNA of the *S. cerevisiae* BY4742 strain as a template, the target DNA fragments were amplified, the DNA fragments were successively bound to each other using the In-Fusion HD Cloning Kit or the like, and the resultant was cloned into the pUC19 vector to prepare the 2 types of target plasmids. The resulting plasmids were designated as pUC-homologous sequence 2-dummy 3-loxP-homologous sequence 5 and pUC-homologous sequence 6-loxP-dummy 4-homologous sequence 3. A set of the 5 types of plasmids comprising pUC-homologous sequence 2-dummy 3-loxP-homologous sequence 5, pUC-homologous sequence 6-loxP-dummy 4-homologous sequence 3, pUC-5U_ADE1-homologous sequence 2 designed in advance (Table 4, FIG. 11), pUC-homologous sequence 2-P_PMA1-nat1-T_LEU2-P_GAL1-Cre-T_CYC1-homologous sequence 3 (Table 5, FIG. 12), and pUC-homologous sequence 3-3U_ADE1 (Table 4, FIG. 11) was designated as the pUC-ade1::loxPout-nat1-Cre (5 fragments) vector set.

TABLE 6

| Amplified DNA fragment | Primer sequence (5'-3') | SEQ ID NO: |
|---|---|---|
| pUC-homologous sequence 2-dummy 3-loxP-homologous sequence 5 | | |
| Fragment containing homologous sequence 2, loxP, 5'-upstream region of PDC6 gene, and homologous sequence 5 | GGGATGGTGTCCCCACAGTTGTCCAGACTACGTCGAATCCTTAC | 105 |
| | GCCTTCACATATAGTATAACTTCGTATAATGTATGCTATACGAACGGTAAAAATTTTGGCCAAATGCCACAGC | 106 |
| Fragment containing pUC19, homologous sequence 2, and homologous sequence 5 | ACTATATGTGAAGGCATGGCTATGGCACGGCAGACATTCCGCCAGATCATCAATAGGCACCAGTCACGACGTTGTAAAACG | 107 |
| | TGGGGACACCATCCCGCCTCAATCACAGGGCGGGAAATAAGCTACAATTAACGCCAAACTCTCAGTACAATCTGCTCTG | 108 |

TABLE 6-continued

| Amplified DNA fragment | Primer sequence (5'-3') | SEQ ID NO: |
|---|---|---|
| pUC-homologous sequence 6-loxP-dummy 4-homologous sequence 3 | | |
| Fragment containing homologous sequence 6, loxP, 3'-downstream region of SED1 gene, and homologous sequence 3 | CTAAGAATGTTCAACATAACTTCGTATAGCATACATTATACG AACGGTACAGTAGTGAAGGCGTCATCCTC | 109 |
| | CAGTCGTAGATGCGTAAAATCGAAAGAAGGCCGCATGAC | 110 |
| Fragment containing pUC19, homologous sequence 6, and homologous sequence e | ACGCATCTACGACTGTGGGTCCCGTGGAGAAATGTATGAAAC CCTGTATGGAGAGTGATTCAGTCACGACGTTGTAAAACGAC | 111 |
| | GTTGAACATTCTTAGGCTGGTCGAATCATTTAGACACGGGCA TCGTCCTCTCGAAAGGTGACTCTCAGTACAATCTGCTCTG | 112 |

Transformation

With the use of the plasmids prepared in the manner described above; i.e., the pUC-gre3::loxPin-G418-Cre vector set; the pUC-gre3::loxPout-G418-Cre vector set; and the pUC-gre3::loxPout-G418-Cre (5 fragments) vector set, as templates, DNA fragments contained in the plasmids were amplified via PCR. The primer sets used in PCR are shown in Table 7. With the use of the amplified DNA fragments, the BY4742 strains were transformed, the transformants were applied to a G418-containing YPD agar medium, and the grown colonies were then naturalized. Strains in which deletion of the GRE3 gene from the chromosome was observed were selected via PCR. Further, the stains were cultured in a YPGa medium (10 g/l yeast extract, 20 g/l peptone, and 20 g/l galactose), Cre gene expression was induced, and the G418 marker and the Cre gene were removed via Cre/loxP site-specific recombination. The resulting strains were designated as Uz3444, Uz3445, and Uz3760 strains. Transformation was performed in accordance with the method of Akada et al. (Akada, R. et al., "Elevated temperature greatly improves transformation of fresh and frozen competent cells in yeast," BioTechniques 28, 2000: 854-856).

With the use of the plasmids; i.e., the pUC-ade1::loxPin-nat1-Cre vector set or the pUC-ade1::loxPout-nat1-Cre vector set, as templates, DNA fragments contained in the plasmids were amplified via PCR. The primer sets used in PCR are shown in Table 7. With the use of the amplified DNA fragments, the Uz3444 or Uz3445 strains were transformed, the transformants were applied to a nourseothricin-containing YPD medium, and colonies were allowed to grow.

With the use of the plasmids; i.e., the pUC-ade1::loxPout-nat1-Cre (5 fragments) vector set, as templates, DNA fragments contained in the plasmids were amplified via PCR. The primer sets used in PCR are shown in Table 7. With the use of the amplified DNA fragments, the BY4742 or Uz3760 strains were transformed, the transformants were applied to a nourseothricin-containing YPD medium, and colonies were allowed to grow. The ADE1 gene is a gene of the adenine biosynthetic pathway. In ADE1-deficient strains, adenine intermediary metabolites; i.e., 5-aminoimidazole riboside, are accumulated, and polymerized polyribosyl aminoimidazole is colored red. Thus, ADE1-deficient strains can be easily identified. The red grown colonies and the white grown colonies were separately counted to inspect the efficiency of the strain comprising the vector set genome introduced thereinto for destructing the ADE1 gene.

TABLE 7

| Amplified DNA fragment | Primer sequence (5'-3') | SEQ ID NO: |
|---|---|---|
| pUC-5U_GRE3-homologous sequence 2 | TGGGGCTAAACGAGATTTGG | 113 |
| | TGGGGACACCATCCCGC | 114 |
| pUC-homologous sequence 2-loxP-P_REG1-G418-T_URA3-T_CYC1-Cre-P_GAL1-loxP-homologous sequenc 3 | AATCACTCTCCATACAGGGTTTCATACATTTCTCC | 116 |
| pUC-homologous sequence 3-3U_GRE3 | ACGCATCTACGACTGTGGGTCC | 117 |
| | GTCTTTTTGCCAGCCAGTCC | 118 |
| pUC-5U_GRE3-loxP-homologous sequence 5 | TGGGGCTAAACGAGATTTGG | 119 |
| | GTGCCTATTGATGATCTGGCGGAATGTCTG | 120 |
| pUC-homologous sequence 5-P_REG1-G418-T_URA3-T_CYC1-Cre-P_GAL1-homologous sequence 6 | ACTATATGTGAAGGCATGGCTATGGCACG | 121 |
| | GTTGAACATTCTTAGGCTGGTCGAATCATTTAGAC | 122 |
| pUC-homologous sequence 6-loxP-3U_GRE3 | CACCTTTCGAGAGGACGATGCCCG | 123 |
| | GTCTTTTTGCCAGCCAGTCC | 124 |
| pUC-homologous sequence 2-dummy 1-loxP-homologous sequence 5 | TTGGCGTTAATTGTAGCTTATTTCCC | 125 |
| | GTGCCTATTGATGATCTGGCGGAATGTCTG | 126 |
| pUC-homologous sequence 6-loxP-dummy 2-homologous sequence 3 | CACCTTTCGAGAGGACGATGCCCG | 127 |
| | AATCACTCTCCATACAGGGTTTCATACATTTCTCC | 128 |
| pUC-5U_ADE1-homologous sequence 2 | ATGAGTCGGGCAATTCCG | 129 |
| | TGGGGACACCATCCCGC | 130 |

TABLE 7-continued

| Amplified DNA fragment | Primer sequence (5'-3') | SEQ ID NO: |
|---|---|---|
| pUC-homologous sequence 2-loxP-<br>P_PMA1-nat1-T_LEU2-P_GAL1-Cre-<br>T_CYC1-loxP-homologous sequence 3 | TTGGCGTTAATTGTAGCTTATTTCCC<br>AATCACTCTCCATACAGGGTTTCATACATTTCTCC | 131<br>132 |
| pUC-homologous sequence<br>3-3U_ADE1 | ACGCATCTACGACTGTGGGTCC<br>TGACCGGATGAAACCACC | 133<br>134 |
| pUC-5U_ADE1-loxP-homologous<br>sequence 5 | ATGAGTCGGGCAATTCCG<br>GTGCCTATTGATGATCTGGCGGAATGTCTG | 135<br>136 |
| pUC-homologous sequence 5-P_PMA1-<br>nat1-T_LEU2-P_GAL1-Cre-T_CYC1-<br>homologous sequence 6 | ACTATATGTGAAGGCATGGCTATGGCACG<br>GTTGAACATTCTTAGGCTGGTCGAATCATTTAGAC | 137<br>138 |
| pUC-homologous sequence 6-loxP-<br>3U_ADE1 | CACCTTTCGAGAGGACGATGCCCG<br>TGACCCGGATGAAACCACC | 139<br>140 |
| pUC-homologous sequence 2-dummy<br>3-loxP-homologous sequence 5 | TTGGCGTTAATTGTAGCTTATTTCCC<br>GTGCCTATTGATGATCTGGCGGAATGTCTG | 141<br>142 |
| pUC-homologous sequence 6-loxP-<br>dummy 4-homologous sequence 3 | CACCTTTCGAGAGGACGATGCCCG<br>AATCACTCTCCATACAGGGTTTCATACATTTCTCC | 143<br>144 |

Results and Discussion

According to the method described in the example, it is necessary that DNA fragments containing loxP accurately undergo homologous recombination to flank the marker gene. Otherwise, it is impossible to remove the marker gene through site-specific recombination with the aid of Cre recombinase (see FIG. 3). According to the method described in the example, whether or not the marker gene had been removed was determined by simply observing the phenotype resulting from marker gene expression without a confirmation process such as PCR.

Meanwhile, according to the method described in the example, the effects achieved by a so-called marker recycle method were verified in the manner described below. Specifically, loxP is provided in each of the DNA fragments adjacent to the DNA fragment that would undergo homologous recombination via the homologous sequence, not in a DNA fragment containing a marker gene. As a result, the marker gene and the homologous sequences flanking the marker gene would be removed from the genome DNA through site-specific recombination by the Cre recombinase. In the case that loxP sequences are provided to flank a marker gene in a DNA fragment comprising the marker gene, in contrast, the marker gene would be removed through site-specific recombination by Cre recombinase, but the homologous sequences flanking the marker gene would not be removed from the genome DNA. When a DNA fragment having the homologous sequences and the marker gene is repeatedly used, accordingly, in the second homologous recombination and thereafter, a homologous sequence remaining after the previous homologous recombination may undergo homologous recombination with the DNA fragment to be repeatedly used. Such homologous recombination may be problematic in practical applications (see FIG. 5).

In order to examine the above problem, at the outset, the pUC-gre3::loxPin-G418-Cre vector set containing a DNA fragment comprising a marker gene flanked by a pair of loxP sequences, and the pUC-gre3::loxPout-G418-Cre vector set containing a DNA fragment comprising a marker gene, other DNA fragments comprising loxP positioned adjacent to the both sides of the aforementioned DNA fragment were intro-duced into the GRE3 gene locus, respectively, and the marker gene was removed via Cre/loxP site-specific recombination to prepare strains (Uz3444, Uz3445). Subsequently, the second homologous recombination was performed. That is, the pUC-ade1::loxPin-nat1-Cre vector set containing a DNA fragment in which a pair of loxP sequences flanks the marker gene, or the pUC-ade1::loxPout-nat1-Cre vector set containing a DNA fragment having a marker gene and DNA fragments positioned adjacent to the both sides of the aforementioned DNA fragment and comprising loxP was introduced into the ADE1 gene locus, and efficiency for homologous recombination was examined.

When a DNA fragment comprising a pair of loxP sequences flanking a marker gene was used, as a result, it was found that repetition of homologous recombination increases the frequency for inaccurate homologous recombination to the extent that practical problems would be caused (Table 8). When a DNA fragment comprising a marker gene and DNA fragments comprising loxP are used, in contrast, it was found that repetition of homologous recombination does not substantially lead to inaccurate homologous recombination. In Table 8, the efficiency for homologous recombination was determined in terms of the red colony count/total colony count.

TABLE 8

| | Marker gene and loxP provided in the same DNA fragment | Marker gene and loxP provided in different DNA fragments |
|---|---|---|
| ADE1-deficient strain<br>Red colony count (homologous recombination efficiency*) | 50(0.532) | 411(0.930) |
| Nourseothricin resistant, non-ADE1-deficient strain<br>White colony | 44 | 31 |

Figure 14:
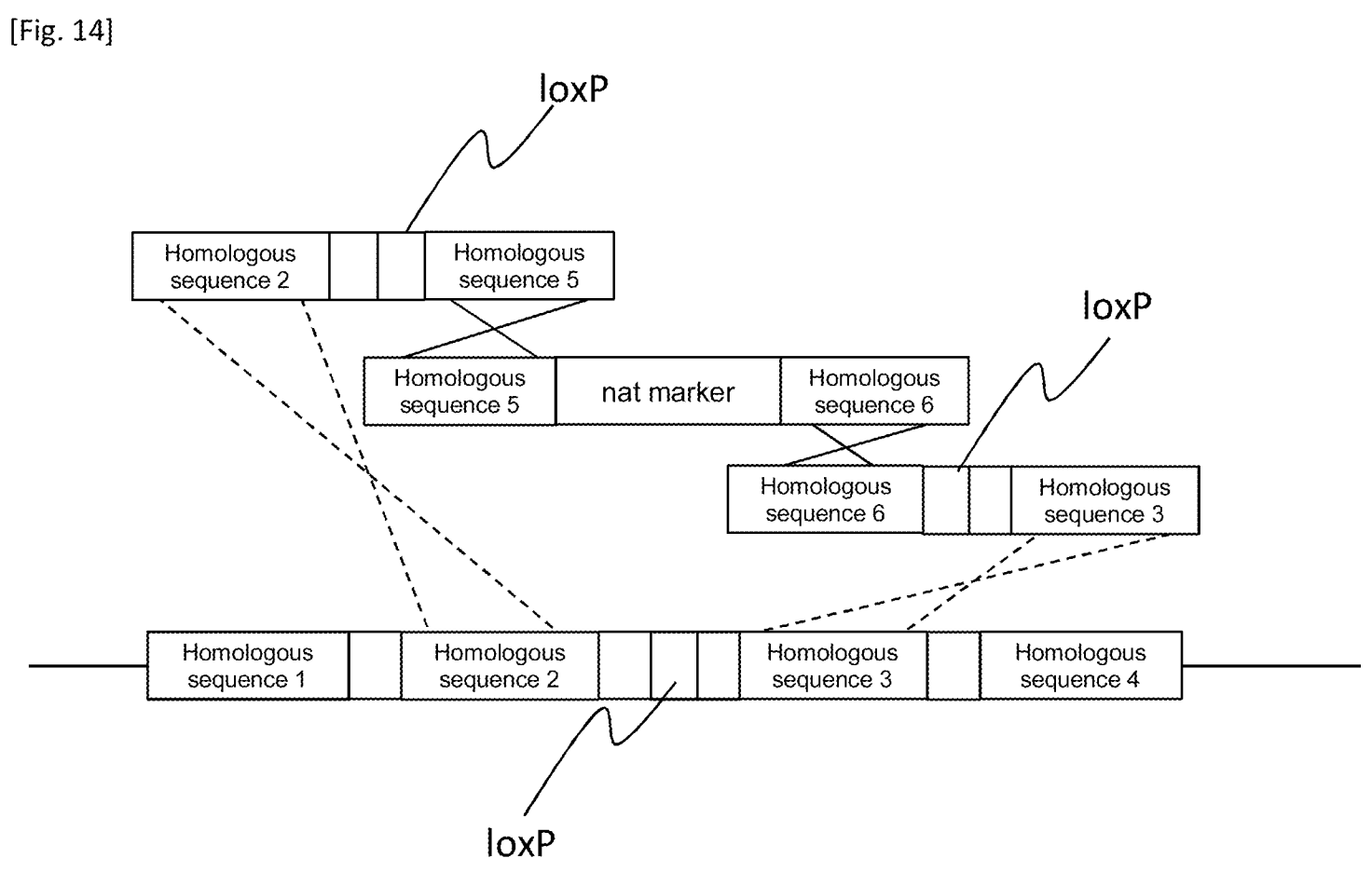

Meanwhile, in the case that the loxP sequences are provided in both DNA fragments adjacent to the DNA fragment comprising a marker gene, in contrast, even if the marker gene flanked by the pair of loxP sequences and homologous sequences are removed, the homologous sequences provided outside the pair of loxP sequences would remain in the genome DNA when the number of DNA fragments is 5 or more (see FIG. 10, the homologous sequences 2 and 3 in FIG. 10). When the marker gene is to be introduced into the ADE1 gene locus in the second recombination (see FIG. 13), homologous recombination may occur between the homologous sequences 2 and 3 remaining in the first GRE3-gene locus and the 3 DNA fragments, as shown in FIG. 14.

In order to examine the possibility described above, at the outset, the pUC-gre3::loxPout-G418-Cre (5 fragments) vector set was introduced into the GRE3 gene locus and the marker gene was removed through Cre/loxP site-specific recombination to prepare a strain of interest (Uz3760). Subsequently, the second homologous recombination was performed. That is, the pUC-ade1::loxPout-nat1-Cre (5 fragments) vector set was introduced into the ADE1 gene locus to prepare a strain of interest. For comparison, a strain selectively comprising the pUC-ade1::loxPout-nat1-Cre (5 fragments) introduced therein was prepared, and the efficiency for homologous recombination was compared.

As a result, no significant differences were observed in the efficiency for homologous recombination as shown in FIG. 9. This indicates that an extent of lowering in the efficiency for homologous recombination caused by repeated use of DNA fragments would be insignificant, provided that the marker gene flanked by a pair of loxP sequences and the homologous sequences are removed. Therefore, the method described in the example can be adopted even if the number of DNA fragments is 5 or more and the applicability of the method is considered extensive.

TABLE 9

|  | An introduction into one locus | Introduction into two loci |
|---|---|---|
| ADE1-deficient strain Red colony count (homologous recombination efficiency*) | 92(0.876) | 84(0.913) |
| Nourseothricin resistant, non-ADE1-deficient strain White colony | 13 | 8 |

The invention claimed is:

1. A method for producing a transformant comprising steps of:
- i) introducing into at least one host cell a first group of three or more nucleic acid fragments having homologous recombination sequences each located at their 5' and 3' ends,
- wherein the first group of nucleic acid fragments comprises:
- a first nucleic acid fragment comprising a target gene, wherein the target gene is a selection marker gene;
- a second nucleic acid fragment in which the homologous recombination sequence at 5' end is either one of a pair of homologous recombination sequences corresponding to a particular region of genome DNA; and
- a third nucleic acid fragment in which the homologous recombination sequence at 3' end is the other of the pair of homologous recombination sequences;
- wherein the nucleic acid fragments constituting the first group of nucleic acid fragments can be linked to each other via the homologous recombination sequence at the end of each nucleic acid fragment, and
- wherein each of a pair of recognition sequences recognized by a site-specific recombinase is comprised in nucleic acid fragments among the first group of nucleic acid fragments, but none of the pair of recognition sequences is comprised in the first nucleic acid fragment comprising the target gene;
- ii) selecting a host cell in which the target gene flanked by the pair of recognition sequences recognized by the site-specific recombinase had been cleaved from genome DNA.

2. The method for producing a transformant according to claim 1, wherein the transformant lacks the particular region of genome DNA upon integration of nucleic acid fragments constituting the first group of nucleic acid fragments therein.

3. The method for producing a transformant according to claim 1, wherein one of the pair of recognition sequences recognized by the site-specific recombinase is comprised in the second nucleic acid fragment, and/or the other of the pair is comprised in the third nucleic acid fragment.

4. The method for producing a transformant according to claim 1,
- wherein the first nucleic acid fragment comprises the target gene between first and second homologous recombination sequences,
- wherein the second nucleic acid fragment comprises the one of the pair of recognition sequences recognized by the site-specific recombinase between third and fourth homologous recombination sequences, wherein the third homologous recombination sequence is at 5' end of the second nucleic acid fragment and the fourth homologous recombination sequence will cause homologous recombination with the first homologous recombination sequence,
- wherein the third nucleic acid fragment comprises the other of the pair of recognition sequences recognized by the site-specific recombinase between fifth and sixth homologous recombination sequences, wherein the sixth homologous recombination sequence is at 3' end of the third nucleic acid fragment and the fifth homologous recombination sequence will cause homologous recombination with the second homologous recombination sequence.

5. The method for producing a transformant according to claim 1,
- wherein the first group of nucleic acid fragments further comprises fourth and fifth nucleic acid fragments having homologous recombination sequences each located at their 5' and 3' ends,
- wherein the first nucleic acid fragment comprises the target gene between first and second homologous recombination sequences, wherein the second nucleic acid fragment comprises a third and fourth homologous recombination sequences at 5' and 3' end of the second nucleic acid fragment, wherein the third nucleic acid fragment comprises a fifth and sixth homologous recombination sequences at 5' and 3' end of the third nucleic acid fragment, wherein the fourth nucleic acid fragment comprises the one of the pair of recognition sequences recognized by the site-specific recombinase between seventh and eighth homologous recombination sequences, wherein the eighth homologous recombination sequence will cause homologous recombination with the first homologous recombination sequence, and the seventh homologous recombination sequence will cause homologous recombination with the fourth homologous recombination sequence, wherein the fifth nucleic acid fragment comprises the other of the pair of recognition sequences recognized by the site-specific recombinase between ninth and tenth homologous recombination sequences, wherein the ninth homologous recombination sequence will cause homologous recombination with the second homologous recombination sequence, and the tenth homologous recombination sequence will cause homologous recombination with the fifth homologous recombination sequence.

6. The method for producing a transformant according to claim 1 further comprising:

i) introducing into the selected host cell a second group of three or more nucleic acid fragments having homologous recombination sequences each located at their 5' and 3' ends, wherein the second group of nucleic acid fragments comprises:

a fourth nucleic acid fragment comprising a target gene, wherein the homologous recombination sequences in the fourth nucleic acid fragment are the same as the homologous recombination sequence in the first nucleic acid fragment;

a fifth nucleic acid fragment in which the homologous recombination sequence at 5' end is either one of a pair of homologous recombination sequences corresponding to the other region of genome DNA, and a sixth nucleic acid fragment in which the homologous recombination sequence at 3' end is the other of the pair of homologous recombination sequences;

wherein the nucleic acid fragments constituting the second group of nucleic acid fragments can be linked to each other via the homologous recombination sequence at the end of each nucleic acid fragment, and wherein each of the pair of recognition sequences recognized by the site-specific recombinase is comprised in nucleic acid fragments among the second group of nucleic acid fragments, but none of the pair of recognition sequences is comprised in the fourth nucleic acid fragment comprising the target gene;

ii) selecting a host cell in which the target gene flanked by the pair of recognition sequences recognized by the site-specific recombinase had been cleaved from genome DNA.

* * * * *